(12) United States Patent
Hansen, Jr. et al.

(10) Patent No.: US 6,828,456 B2
(45) Date of Patent: Dec. 7, 2004

(54) 2-AMINO-2-ALKYL-3 HEXENOIC AND HEXYNOIC ACID DERIVATIVES USEFUL AS NITRIC OXIDE SYNTHASE INHIBITORS

(75) Inventors: Donald W. Hansen, Jr., Skokie, IL (US); Ronald Keith Webber, St. Charles, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/954,988

(22) Filed: Sep. 15, 2001

(65) Prior Publication Data

US 2002/0072631 A1 Jun. 13, 2002

Related U.S. Application Data

(60) Provisional application No. 60/232,816, filed on Sep. 15, 2000.

(51) Int. Cl.[7] .................... C07C 255/00; C07C 291/00; C07C 229/00
(52) U.S. Cl. ................. 558/442; 562/560; 562/561
(58) Field of Search ................ 562/560, 561, 562/564; 558/442

(56) References Cited

U.S. PATENT DOCUMENTS

| 5,132,453 A | 7/1992 | Griffith | ........ 562/560 |
| 6,344,483 B1 * | 2/2002 | Hallinan et al. | |

FOREIGN PATENT DOCUMENTS

| WO | WO 9313055 | 7/1993 | ......... C07C/257/14 |
| WO | WO 9324126 | 12/1993 | ......... A61K/31/395 |
| WO | WO 9525717 | 9/1995 | ......... C07C/257/14 |
| WO | WO 95/25717 A1 * | 10/1995 | |

OTHER PUBLICATIONS

Beaulieu et al, Synthesis of Chiral Vinylglycines, 1991, Journal of Organic Chemistry, 56, pp. 4196–4204.*
Misko, et al., *European Journal of Pharmacology*; 223: 119–125 (1993).
Lee, et al, *Bioorganic Med. Chemistry*; 7(6): 1097–1104 (1999).
Young et al., *Bioorganic Med. Chemistry Letters*; 10(6): 597–600 (2000).
Greene, Theodora & Wuts, Peter. *Protective Groups in Organic Synthesis. 3rd Edit.*; John Wiley & Sons, New York, (1999), pp. 494–653.
Bredt & Synder, *Proceedings of the National Academy of Science USA*; 87: 682–685 (1990).
Moore et al., *Journal of Medicinal Chemistry*; 39(3): 669–672 (1996).
Rodi et al., *The Biology of Nitric Oxide, Part 4: Enzymology, Biochemsitry, & Immunology: Moncada, S; Freelisch, M; Busse, R; Higgs, E, Eds.*; Portland Press Ltd., London, (1995) pp 447–450.
Misko, et al., *Analytical Biochemistry*; 214(1): 11–16 (1993).
Moncada, S. & Higgs, E., *FASEB Journal*; 9: 1319–1330 (1995).

* cited by examiner

Primary Examiner—Paul A. Zucker
(74) Attorney, Agent, or Firm—Philip B. Polster, II

(57) ABSTRACT

The present invention relates to 2-amino-2-alkyl-3 hexenoic and hexynoic acid derivatives and their use in therapy, in particular their use as nitric oxide synthase inhibitors.

104 Claims, No Drawings

2-AMINO-2-ALKYL-3 HEXENOIC AND HEXYNOIC ACID DERIVATIVES USEFUL AS NITRIC OXIDE SYNTHASE INHIBITORS

CROSS REFERENCE TO RELATED APPLICATIONS

This application claims the benefit of U.S. Provisional Application Ser. No. 60/232,816, filed Sep. 15, 2000.

FIELD OF THE INVENTION

The present invention relates to 2-amino-2-alkyl-3 hexenoic and hexynoic acid derivatives and their use in therapy, in particular their use as nitric oxide synthase inhibitors.

RELATED ART

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:
(i) a constitutive, $Ca^{++}$/calmodulin dependent enzyme, located in the endothelium, that releases NO in response to receptor or physical stimulation.
(ii) a constitutive, $Ca^{++}$/calmodulin dependent enzyme, located in the brain, that releases NO in response to receptor or physical stimulation.
(iii) a $Ca^{++}$ independent enzyme which is induced after activation of vascular smooth muscle, macrophages, endothelial cells, and a number of other cells by endotoxin and cytokines. Once expressed, this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase, such consequences including hypertension and possible thrombosis and tissue damage. In particular, in the case of the therapeutic use of L-NMMA (a non-selective NO synthase inhibitor) for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

PCT International Publication No. WO 93/13055 and U.S. Pat. No. 5,132,453, the disclosure of which are hereby incorporated by reference in their entirety as if written herein, disclose compounds that inhibit nitric oxide synthesis and preferentially inhibit the inducible isoform of nitric oxide synthase.

PCT International Publication No. WO 95/25717 discloses certain amidino derivatives as being useful in inhibiting inducible nitric oxide synthase.

Various attempts have been made to improve the potency and selectivity of NOS inhibitors by adding one or more rigidifying elements to the inhibitor's structure. Publications by Y. Lee et al (*Bioorg. Med. Chem.* 7, 1097 (1999)) and R. J. Young et al (*Bioorg. Med. Chem. Lett.* 10, 597 (2000)) teach that imposing conformational rigidity with one or more carbon-carbon double bonds is not a favorable approach to impart selectivity for NOS inhibitors.

SUMMARY OF THE INVENTION

Compounds have now been found which have the advantage of being very efficacious in the human cartilage explant assay, a model for osteoarthritis.

The present invention teaches that a carbon-carbon double bond can be used as a rigidifying element, and the resulting compounds will have unexpected potency and selectivity for inhibition of inducible NOS.

The present disclosure teaches that a carbon-carbon double bond imparts a favorable interaction with inducible NOS, such that the resulting compounds have unexpected potency and selectivity for inhibition of inducible NOS over the constitutive isoforms.

Further, compounds of the present invention have the advantage of being very efficacious as iNOS inhibitors in the human cartilage explant assay, a model for osteoarthritis. At the same time the compounds of the present invention are surprisingly less able to penetrate certain non-target organs in test systems, especially in comparison to the compounds of WO 93/13055. This surprising differentiation in expected access between the target organ (cartilage) and other organs is an unexpected advantage for the compounds of the present invention.

In a broad aspect, compounds of the present invention are represented by:

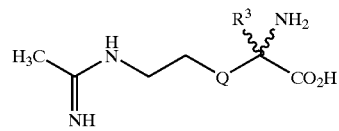

-continued

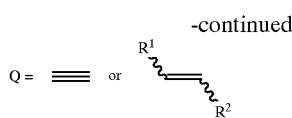

or a pharmaceutically acceptable salt thereof, wherein:
 $R^1$ is selected from the group consisting of hydrogen, halo, $C_1$–$C_5$ alkyl and $C_1$–$C_5$ alkyl substituted by alkoxy or one or more halo;
 $R^2$ is selected from the group consisting of hydrogen, halo, $C_1$–$C_5$ alkyl and $C_1$–$C_5$ alkyl substituted by alkoxy or one or more halo;
 $R^3$ is $C_1$–$C_5$ alkyl or $C_1$–$C_5$ alkyl substituted by alkoxy or one or more halo.

In an embodiment represented by Formula I, the invention relates to:

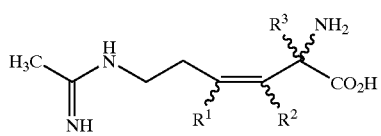

I or a pharmaceutically acceptable salt thereof, wherein:
 $R^1$ is selected from the group consisting of hydrogen, halo, $C_1$–$C_5$ alkyl and $C_1$–$C_5$ alkyl substituted by alkoxy or one or more halo;
 $R^2$ is selected from the group consisting of hydrogen, halo, $C_1$–$C_5$ alkyl and $C_1$–$C_5$ alkyl substituted by alkoxy or one or more halo;
 $R^3$ is $C_1$–$C_5$ alkyl or $C_1$–$C_5$ alkyl substituted by alkoxy or one or more halo.

In an embodiment represented by Formula II, the invention relates to:

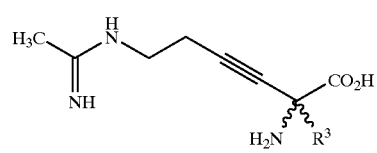

II or a pharmaceutically acceptable salt thereof, wherein:
 $R^3$ is $C_1$–$C_5$ alkyl, said $C_1$–$C_5$ alkyl optionally substituted by halo or alkoxy, said alkoxy optionally substituted by one or more halo.

In an embodiment represented by Formula III, the invention relates to:

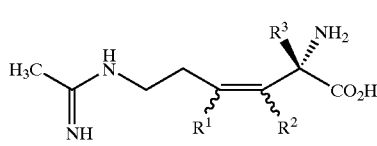

III or a pharmaceutically acceptable salt thereof, wherein:
 $R^1$ is selected from the group consisting of hydrogen, halo, $C_1$–$C_5$ alkyl and $C_1$–$C_5$ alkyl substituted by alkoxy or one or more halo;
 $R^2$ is selected from the group consisting of hydrogen, halo, $C_1$–$C_5$ alkyl and $C_1$–$C_5$ alkyl substituted by alkoxy or one or more halo;
 $R^3$ is $C_1$–$C_5$ alkyl or $C_1$–$C_5$ alkyl substituted by alkoxy or one or more halo.

In an embodiment represented by Formula IV, the invention relates to:

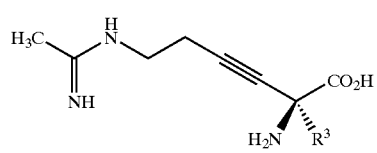

IV or a pharmaceutically acceptable salt thereof, wherein:
 $R^3$ is $C_1$–$C_5$ alkyl or $C_1$–$C_5$ alkyl substituted by alkoxy or one or more halo.

In an embodiment represented by Formula V, the invention relates to:

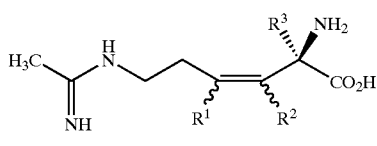

V or a pharmaceutically acceptable salt thereof, wherein:
 $R^1$ is selected from the group consisting of hydrogen, halo, $C_1$–$C_5$ alkyl and $C_1$–$C_5$ alkyl substituted by alkoxy or one or more halo;
 $R^2$ is selected from the group consisting of hydrogen, halo, $C_1$–$C_5$ alkyl and $C_1$–$C_5$ alkyl substituted by alkoxy or one or more halo;
 $R^3$ is $C_1$–$C_5$ alkyl or $C_1$–$C_5$ alkyl substituted by alkoxy or one or more halo.

In an embodiment represented by Formula VI, the invention relates to:

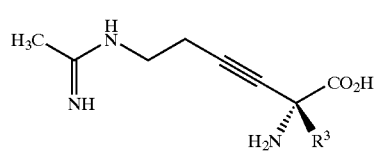

VI or a pharmaceutically acceptable salt thereof, wherein:
 $R^3$ is $C_1$–$C_5$ alkyl or $C_1$–$C_5$ alkyl substituted by alkoxy or one or more halo.

In a broad aspect, the present invention is directed to novel compounds, pharmaceutical compositions, process for preparing novel compounds, process for preparing pharmaceutical compositions, and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part.

Compounds of the present invention will be useful for treating, among other things, inflammation in a subject, or for treating other nitric oxide synthase-mediated disorders, such as, as an analgesic in the treatment of pain and headaches. The compounds of the present invention will be useful in the treatment of pain including somatogenic (either nociceptive or neuropathic), both acute and chronic, and could be used in a situation including neuropathic pain for which a common NSAID, opioid analgesic or certain anticonvulsants would traditionally be administered.

Included within the scope of the present invention are novel intermediates useful for synthesizing compounds of the present invention.

Conditions in which the compounds of the present invention will provide an advantage in inhibiting NO production from L-arginine include arthritic conditions. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and post-operative inflammation including inflammation from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis.

Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like.

The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. These compounds would also be useful in the treatment of allergic rhinitis, respiratory distress syndrome, endotoxin shock syndrome, and atherosclerosis. The compounds would also be useful in the treatment of pain, including but not limited to postoperative pain, dental pain, muscular pain, pain caused by temporomandibular joint syndrome, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals and other vertebrates. More preferred animals include horses, dogs, and cats.

The present compounds may also be used in co-therapies, partially or completely, in place of other conventional anti-inflammatory therapies, such as together with steroids, NSAIDs, COX-2 selective inhibitors, matrix metalloproteinase inhibitors, 5-lipoxygenase inhibitors, $LTB_4$ antagonists and $LTA_4$ hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia, such as, for example pre-senile dementia, and AIDS-related dementia, cachexia, Sydenham's chorea, Huntington's disease, Amyotrophic Lateral Sclerosis, Korsakoff s disease, imbecility relating to a cerebral vessel disorder, sleeping disorders, schizophrenia, depression, depression or other symptoms associated with Premenstrual Syndrome (PMS), anxiety and septic shock.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

Compounds of the invention are useful for the prevention or treatment of cancer, such as colorectal cancer, and cancer of the breast, lung, prostate, bladder, cervix and skin. The present invention is further directed to the use of the compounds of the present invention for the treatment and prevention of neoplasias. The neoplasias that will be treatable or preventable by the compounds and methods of the present invention include brain cancer, bone cancer, a leukemia, such as, for example chronic lymphocytic leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, urogenital cancers, such as ovary cancer, cervical cancer, vulvar cancer, and lung cancer, breast cancer and skin cancer, such as squamous cell, melanoma, and basal cell cancers, prostate cancer, renal cell carcinoma, and other known cancers that effect epithelial cells throughout the body. Compounds of the present invention will be effective as well for treatment of mesenchymal derived neoplasias. Preferably, the neoplasia to be treated is selected from gastrointestinal cancer, liver cancer, bladder cancer, pancreas cancer, ovary cancer, prostate cancer, cervical cancer, vulvar cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko $DC_{89}$-A1, Kyowa Hakko $DC_{92}$-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharnar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation; latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid).

A further embodiment provides a therapeutic combination of a compound of the present invention with an opioid compound. Opioid compounds useful in this combination include without limitation morphine, methadone, hydromorphone, oxymorphone, levorphanol, levallorphan, codeine, dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, nor-binaltorphimine, naltrindole, DPDPE, [D-la$^2$, glu$^4$]deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

DETAILED DESCRIPTION OF THE INVENTION

In an embodiment represented by Formula I, the invention relates to:

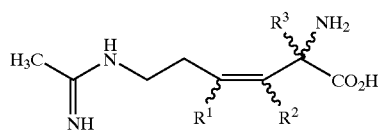

I or a pharmaceutically acceptable salt thereof, wherein:
$R^1$ is selected from the group consisting of hydrogen, halo, $C_1$–$C_5$ alkyl and $C_1$–$C_5$ alkyl substituted by alkoxy or one or more halo;
$R^2$ is selected from the group consisting of hydrogen, halo, $C_1$–$C_5$ alkyl and $C_1$–$C_5$ alkyl substituted by alkoxy or one or more halo;
$R^3$ is $C_1$–$C_5$ alkyl or $C_1$–$C_5$ alkyl substituted by alkoxy or one or more halo.

In one embodiment of the present invention represented by Formula I, the compound is the Z isomer.

In another embodiment of the present invention represented by Formula I, the compound is the E isomer.

In yet another embodiment of the present invention represented by Formula I, $R^1$ is hydrogen, halo, or $C_1$–$C_5$ alkyl, said $C_1$–$C_5$ alkyl optionally substituted by halo or alkoxy, said alkoxy optionally substituted by one or more halo; $R^2$ is hydrogen, halo or $C_1$–$C_5$ alkyl, said $C_1$–$C_5$ alkyl optionally substituted by halo or alkoxy, said alkoxy optionally substituted by one or more halo; and $R^3$ is $C_1$–$C_5$ alkyl, said $C_1$–$C_5$ alkyl optionally substituted by halo or alkoxy.

In another embodiment of the present invention represented by Formula I, $R^1$ is hydrogen, halo, or $C_1$–$C_3$ alkyl; $R^2$ is hydrogen, halo or $C_1$–$C_3$ alkyl; and $R^3$ is $C_1$–$C_5$ alkyl, said $C_1$–$C_5$ alkyl optionally substituted by fluorine or alkoxy.

In a further embodiment of the present invention represented by Formula I, $R^1$ is hydrogen, halo, or $C_1$–$C_3$ alkyl; $R^2$ is hydrogen, halo or $C_1$–$C_3$ alkyl; and $R^3$ is $C_1$–$C_3$ alkyl.

In another embodiment of the present invention represented by Formula I, $R^1$ is hydrogen; $R^2$ is hydrogen, halo or $C_1$–$C_3$ alkyl; and $R^3$ is $C_1$–$C_3$ alkyl.

In a still further embodiment of the present invention represented by Formula I, $R^1$ is hydrogen; $R^2$ is hydrogen or halo; and $R^3$ is $C_1$–$C_3$ alkyl.

In another embodiment of the present invention represented by Formula I, $R^1$ is hydrogen; $R^2$ is hydrogen or fluorine; and $R^3$ is $C_1$–$C_3$ alkyl.

In another embodiment of the present invention represented by Formula I, $R^1$ is hydrogen; $R^2$ is hydrogen or fluorine; and $R^3$ is methyl.

In another embodiment of the present invention represented by Formula I, $R^1$ is hydrogen; $R^2$ is hydrogen; and $R^3$ is methyl.

In a further embodiment of the present invention represented by Formula I, $R^1$ is hydrogen; $R^2$ is fluorine; and $R^3$ is methyl.

In another embodiment of the present invention represented by Formula I, $R^1$ is halo; $R^2$ is hydrogen, halo or $C_1$–$C_3$ alkyl; and $R^3$ is $C_1$–$C_3$ alkyl.

In a further embodiment of the present invention represented by Formula I, $R^1$ is halo; $R^2$ is halo; and $R^3$ is $C_1$–$C_3$ alkyl.

In another embodiment of the present invention represented by Formula I, $R^1$ is fluorine; $R^2$ is fluorine; and $R^3$ is methyl.

In another embodiment of the present invention represented by Formula I, $R^1$ is fluorine; $R^2$ is hydrogen or $C_1$–$C_3$ alkyl; and $R^3$ is methyl.

In a further embodiment of the present invention represented by Formula I, $R^1$ is fluorine; $R^2$ is hydrogen; and $R^3$ is methyl.

In another embodiment of the present invention represented by Formula I, $R^1$ is methyl; $R^2$ is hydrogen; and $R^3$ is methyl.

In a further embodiment of the present invention represented by Formula I, $R^1$ is hydrogen; $R^2$ is methyl; and $R^3$ is methyl.

In another embodiment of the present invention represented by Formula I, $R^1$ is methyl; $R^2$ is methyl; and $R^3$ is methyl.

In yet another embodiment of the present invention represented by Formula I,: $R^1$ is hydrogen, halo or $C_1$–$C_5$ alkyl, said $C_1$–$C_5$ alkyl optionally substituted by alkoxy or one or more fluorine; $R^2$ is hydrogen, halo or $C_1$–$C_5$ alkyl, said $C_1$–$C_5$ alkyl optionally substituted by alkoxy or one or more fluorine; and $R^3$ is methyl optionally substituted by one or more alkoxy or halo.

In a further embodiment of the present invention represented by Formula I, $R^1$ is hydrogen or fluorine; $R^2$ is $C_1$–$C_3$ alkyl substituted by one or more halo; and $R^3$ is methyl.

In another embodiment of the present invention represented by Formula I, $R^1$ is hydrogen; $R^2$ is $CH_2F$; and $R^3$ is methyl.

In still another embodiment of the present invention represented by Formula I, $R^1$ is $CH_2F$; $R^2$ is hydrogen; and $R^3$ is methyl.

In a further embodiment of the present invention represented by Formula I, $R^1$ is hydrogen; $R^2$ is hydrogen; and $R^3$ is $CH_2F$.

In another embodiment of the present invention represented by Formula I, $R^1$ is hydrogen; $R^2$ is methoxymethyl; and $R^3$ is methyl.

In a further embodiment of the present invention represented by Formula I, $R^1$ is methoxymethyl; $R^2$ is hydrogen; and $R^3$ is methyl.

In another embodiment of the present invention represented by Formula I, $R^1$ is hydrogen; $R^2$ is hydrogen; and $R^3$ is methoxymethyl.

In an embodiment represented by Formula II, the invention relates to:

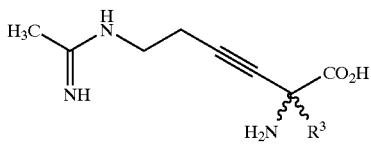

II or a pharmaceutically acceptable salt thereof, wherein:
  $R^3$ is $C_1$–$C_5$ alkyl, said $C_1$–$C_5$ alkyl optionally substituted by halo or alkoxy, said alkoxy optionally substituted by one or more halo.

In another embodiment of the present invention represented by Formula II, $R^3$ is $C_1$–$C_5$ alkyl substituted by one or more halo.

In a further embodiment of the present invention represented by Formula II, $R^3$ is $C_1$–$C_5$ alkyl substituted by one or more fluorine.

In still another embodiment of the present invention represented by Formula II, $R^3$ is methyl substituted by one or more halo.

In yet another embodiment of the present invention represented by Formula II, $R^3$ is methyl substituted by one or more fluorine. In another embodiment of the present invention represented by Formula II, $R^3$ is $CH_2F$.

In still another embodiment of the present invention represented by Formula II, $R^3$ is $C_1$–$C_5$ alkyl substituted by alkoxy.

In a further embodiment of the present invention represented by Formula II, $R^3$ is methoxy methyl.

In yet another embodiment of the present invention represented by Formula II, $R^3$ is $C_1$–$C_5$ alkyl.

In another embodiment of the present invention represented by Formula II, $R^3$ is methyl.

In an embodiment represented by Formula III, the invention relates to:

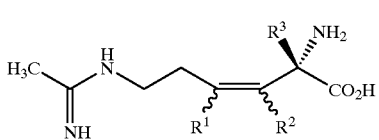

III or a pharmaceutically acceptable salt thereof, wherein:
  $R^1$ is selected from the group consisting of hydrogen, halo, $C_1$–$C_5$ alkyl and $C_1$–$C_5$ alkyl substituted by alkoxy or one or more halo;
  $R^2$ is selected from the group consisting of hydrogen, halo, $C_1$–$C_5$ alkyl and $C_1$–$C_5$ alkyl substituted by alkoxy or one or more halo;
  $R^3$ is $C_1$–$C_5$ alkyl or $C_1$–$C_5$ alkyl substituted by alkoxy or one or more halo.

In one embodiment of the present invention represented by Formula III, the compound is the Z isomer.

In another embodiment of the present invention represented by Formula III, the compound is the E isomer.

In yet another embodiment of the present invention represented by Formula III, $R^1$ is hydrogen, halo, or $C_1$–$C_5$ alkyl, said $C_1$–$C_5$ alkyl optionally substituted by halo or alkoxy, said alkoxy optionally substituted by one or more halo; $R^2$ is hydrogen, halo or $C_1$–$C_5$ alkyl, said $C_1$–$C_5$ alkyl optionally substituted by halo or alkoxy, said alkoxy optionally substituted by one or more halo; and $R^3$ is C 5–$C_5$ alkyl, said $C_1$–$C_5$ alkyl optionally substituted by halo or alkoxy.

In another embodiment of the present invention represented by Formula III, $R^1$ is hydrogen, halo, or $C_1$–$C_3$ alkyl; $R^2$ is hydrogen, halo or $C_1$–$C_3$ alkyl; and $R^3$ is $C_1$–$C_5$ alkyl, said $C_1$–$C_5$ alkyl optionally substituted by fluorine or alkoxy.

In a further embodiment of the present invention represented by Formula III, $R^1$ is hydrogen, halo, or $C_1$–$C_3$ alkyl; $R^2$ is hydrogen, halo or $C_1$–$C_3$ alkyl; and $R^3$ is $C_1$–$C_3$ alkyl.

In another embodiment of the present invention represented by Formula III, $R^1$ is hydrogen; $R^2$ is hydrogen, halo or $C_1$–$C_3$ alkyl; and $R^3$ is $C_1$–$C_3$ alkyl.

In a still further embodiment of the present invention represented by Formula III, $R^1$ is hydrogen; $R^2$ is hydrogen or halo; and $R^3$ is $C_1$–$C_3$ alkyl.

In another embodiment of the present invention represented by Formula III, $R^1$ is hydrogen; $R^2$ is hydrogen or fluorine; and $R^3$ is $C_1$–$C_3$ alkyl.

In another embodiment of the present invention represented by Formula III, $R^1$ is hydrogen; $R^2$ is hydrogen or fluorine; and $R^3$ is methyl.

In another embodiment of the present invention represented by Formula III, $R^1$ is hydrogen; $R^2$ is hydrogen; and $R^3$ is methyl.

In a further embodiment of the present invention represented by Formula III, $R^1$ is hydrogen; $R^2$ is fluorine; and $R^3$ is methyl.

In another embodiment of the present invention represented by Formula III, $R^1$ is halo; $R^2$ is hydrogen, halo or $C_1$–$C_3$ alkyl; and $R^3$ is $C_1$–$C_3$ alkyl.

In a further embodiment of the present invention represented by Formula III, $R^1$ is halo; $R^2$ is halo; and $R^3$ is $C_1$–$C_3$ alkyl.

In another embodiment of the present invention represented by Formula III, $R^1$ is fluorine; $R^2$ is fluorine; and $R^3$ is methyl.

In another embodiment of the present invention represented by Formula III, $R^1$ is fluorine; $R^2$ is hydrogen or $C_1$–$C_3$ alkyl; and $R^3$ is methyl.

In a further embodiment of the present invention represented by Formula III, $R^1$ is fluorine; $R^2$ is hydrogen; and $R^3$ is methyl.

In another embodiment of the present invention represented by Formula III, $R^1$ is methyl; $R^2$ is hydrogen; and $R^3$ is methyl.

In a further embodiment of the present invention represented by Formula III, $R^1$ is hydrogen; $R^2$ is methyl; and $R^3$ is methyl.

In another embodiment of the present invention represented by Formula III, $R^1$ is methyl; $R^2$ is methyl; and $R^3$ is methyl.

In yet another embodiment of the present invention represented by Formula III,: $R^1$ is hydrogen, halo or $C_1$–$C_5$ alkyl, said $C_1$–$C_5$ alkyl optionally substituted by alkoxy or one or more fluorine; $R^2$ is hydrogen, halo or $C_1$–$C_5$ alkyl, said $C_1$–$C_5$ alkyl optionally substituted by alkoxy or one or more fluorine; and $R^3$ is methyl optionally substituted by one or more alkoxy or halo.

In a further embodiment of the present invention represented by Formula III, $R^1$ is hydrogen or fluorine; $R^2$ is $C_1$–$C_3$ alkyl substituted by one or more halo; and $R^3$ is methyl.

In another embodiment of the present invention represented by Formula III, $R^1$ is hydrogen; $R^2$ is $CH_2F$; and $R^3$ is methyl.

In still another embodiment of the present invention represented by Formula III, $R^1$ is $CH_2F$; $R^2$ is hydrogen; and $R^3$ is methyl.

In a further embodiment of the present invention represented by Formula III, $R^1$ is hydrogen; $R^2$ is hydrogen; and $R^3$ is $CH_2F$.

In another embodiment of the present invention represented by Formula III, $R^1$ is hydrogen; $R^2$ is methoxymethyl; and $R^3$ is methyl.

In a further embodiment of the present invention represented by Formula III, $R^1$ is methoxymethyl; $R^2$ is hydrogen; and $R^3$ is methyl.

In another embodiment of the present invention represented by Formula III, $R^1$ is hydrogen; $R^2$ is hydrogen; and $R^3$ is methoxymethyl.

In an embodiment represented by Formula IV, the invention relates to:

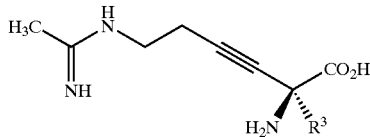

IV or a pharmaceutically acceptable salt thereof, wherein:
$R^3$ is $C_1$–$C_5$ alkyl or $C_1$–$C_5$ alkyl substituted by alkoxy or one or more halo.

In another embodiment of the present invention represented by Formula II, $R^3$ is $C_1$–$C_5$ alkyl substituted by one or more halo.

In a further embodiment of the present invention represented by Formula II $R^3$ is $C_1$–$C_5$ alkyl substituted by one or more fluorine.

In still another embodiment of the present invention represented by Formula II, $R^3$ is methyl substituted by one or more halo.

In yet another embodiment of the present invention represented by Formula II, $R^3$ is methyl substituted by one or more fluorine. In another embodiment of the present invention represented by Formula III, $R^3$ is $CH_2F$.

In still another embodiment of the present invention represented by Formula II, $R^3$ is $C_1$–$C_5$ alkyl substituted by alkoxy.

In a further embodiment of the present invention represented by Formula II, $R^3$ is methoxy methyl.

In yet another embodiment of the present invention represented by Formula II, $R^3$ is $C_1$–$C_5$ alkyl.

In another embodiment of the present invention represented by Formula II, $R^3$ is methyl.

In an embodiment represented by Formula V, the invention relates to:

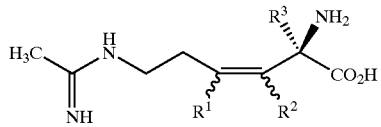

V or a pharmaceutically acceptable salt thereof, wherein:
$R^1$ is selected from the group consisting of hydrogen, halo, $C_1$–$C_5$ alkyl and $C_1$–$C_5$ alkyl substituted by alkoxy or one or more halo;
$R^2$ is selected from the group consisting of hydrogen, halo, $C_1$–$C_5$ alkyl and $C_1$–$C_5$ alkyl substituted by alkoxy or one or more halo;
$R^3$ is $C_1$–$C_5$ alkyl or $C_1$–$C_5$ alkyl substituted by alkoxy or one or more halo.

In one embodiment of the present invention represented by Formula V, the compound is the Z isomer.

In another embodiment of the present invention represented by Formula V, the compound is the E isomer.

In yet another embodiment of the present invention represented by Formula V, $R^1$ is hydrogen, halo, or $C_1$–$C_5$ alkyl, said $C_1$–$C_5$ alkyl optionally substituted by halo or alkoxy, said alkoxy optionally substituted by one or more halo; $R^2$ is hydrogen, halo or $C_1$–$C_5$ alkyl, said $C_1$–$C_5$ alkyl optionally substituted by halo or alkoxy, said alkoxy optionally substituted by one or more halo; and $R^3$ is $C_1$–$C_5$ alkyl, said $C_1$–$C_5$ alkyl optionally substituted by halo or alkoxy.

In another embodiment of the present invention represented by Formula V, $R^1$ is hydrogen, halo, or $C_1$–$C_3$ alkyl; $R^2$ is hydrogen, halo or $C_1$–$C_3$ alkyl; and $R^3$ is $C_1$–$C_5$ alkyl, said $C_1$–$C_5$ alkyl optionally substituted by fluorine or alkoxy.

In a further embodiment of the present invention represented by Formula V, $R^1$ is hydrogen, halo, or $C_1$–$C_3$ alkyl; $R^2$ is hydrogen, halo or $C_1$–$C_3$ alkyl; and $R^3$ is $C_1$–$C_3$ alkyl.

In another embodiment of the present invention represented by Formula V, $R^1$ is hydrogen; $R^2$ is hydrogen, halo or $C_1$–$C_3$ alkyl; and $R^3$ is $C_1$–$C_3$ alkyl.

In a still further embodiment of the present invention represented by Formula V, $R^1$ is hydrogen; $R^2$ is hydrogen or halo; and $R^3$ is $C_1$–$C_3$ alkyl.

In another embodiment of the present invention represented by Formula V, $R^1$ is hydrogen; $R^2$ is hydrogen or fluorine; and $R^3$ is $C_1$–$C_3$ alkyl.

In another embodiment of the present invention represented by Formula V, $R^1$ is hydrogen; $R^2$ is hydrogen or fluorine; and $R^3$ is methyl.

In another embodiment of the present invention represented by Formula V, $R^1$ is hydrogen; $R^2$ is hydrogen; and $R^3$ is methyl.

In a further embodiment of the present invention represented by Formula V, $R^1$ is hydrogen; $R^2$ is fluorine; and $R^3$ is methyl.

In another embodiment of the present invention represented by Formula V, $R^1$ is halo; $R^2$ is hydrogen, halo or $C_1$–$C_3$ alkyl; and $R^3$ is $C_1$–$C_3$ alkyl.

In a further embodiment of the present invention represented by Formula V, $R^1$ is halo; $R^2$ is halo; and $R^3$ is $C_1$–$C_3$ alkyl.

In another embodiment of the present invention represented by Formula V, $R^1$ is fluorine; $R^2$ is fluorine; and $R^3$ is methyl.

In another embodiment of the present invention represented by Formula V, $R^1$ is fluorine; $R^2$ is hydrogen or $C_1$–$C_3$ alkyl; and $R^3$ is methyl.

In a further embodiment of the present invention represented by Formula V, $R^1$ is fluorine; $R^2$ is hydrogen; and $R^3$ is methyl.

In another embodiment of the present invention represented by Formula V, $R^1$ is methyl; $R^2$ is hydrogen; and $R^3$ is methyl.

In a further embodiment of the present invention represented by Formula V, $R^1$ is hydrogen; $R^2$ is methyl; and $R^3$ is methyl.

In another embodiment of the present invention represented by Formula V, $R^1$ is methyl; $R^2$ is methyl; and $R^3$ is methyl.

In yet another embodiment of the present invention represented by Formula V,: $R^1$ is hydrogen, halo or $C_1$–$C_5$ alkyl, said $C_1$–$C_5$ alkyl optionally substituted by alkoxy or one or more fluorine; $R^2$ is hydrogen, halo or $C_1$–$C_5$ alkyl, said $C_1$–$C_5$ alkyl optionally substituted by alkoxy or one or more fluorine; and $R^3$ is methyl optionally substituted by one or more alkoxy or halo.

In a further embodiment of the present invention represented by Formula V, $R^1$ is hydrogen or fluorine; $R^2$ is $C_1$–$C_3$ alkyl substituted by one or more halo; and $R^3$ is methyl.

In another embodiment of the present invention represented by Formula V, $R^1$ is hydrogen; $R^2$ is $CH_2F$; and $R^3$ is methyl.

In still another embodiment of the present invention represented by Formula V, $R^1$ is $CH_2F$; $R^2$ is hydrogen; and $R^3$ is methyl.

In a further embodiment of the present invention represented by Formula V, $R^1$ is hydrogen; $R^2$ is hydrogen; and $R^3$ is $CH_2F$.

In another embodiment of the present invention represented by Formula V, $R^1$ is hydrogen; $R^2$ is methoxymethyl; and $R^3$ is methyl.

In a further embodiment of the present invention represented by Formula V, $R^1$ is methoxymethyl; $R^2$ is hydrogen; and $R^3$ is methyl.

In another embodiment of the present invention represented by Formula V, $R^1$ is hydrogen; $R^2$ is hydrogen; and $R^3$ is methoxymethyl.

In an embodiment represented by Formula VI, the invention relates to:

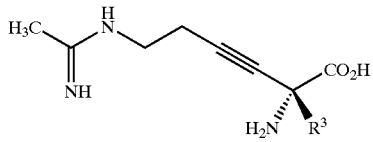

VI or a pharmaceutically acceptable salt thereof, wherein:
$R^3$ is $C_1$–$C_5$ alkyl or $C_1$–$C_5$ alkyl substituted by alkoxy or one or more halo.

In another embodiment of the present invention represented by Formula VI, $R^3$ is $C_1$–$C_5$ alkyl substituted by one or more halo.

In a further embodiment of the present invention represented by Formula VI, $R^3$ is $C_1$–$C_5$ alkyl substituted by one or more fluorine.

In still another embodiment of the present invention represented by Formula VI, $R^3$ is methyl substituted by one or more halo.

In yet another embodiment of the present invention represented by Formula VI, $R^3$ is methyl substituted by one or more fluorine. In another embodiment of the present invention represented by Formula VI, $R^3$ is $CH_2F$.

In still another embodiment of the present invention represented by Formula VI, $R^3$ is $C_1$–$C_5$ alkyl substituted by alkoxy.

In a further embodiment of the present invention represented by Formula VI, $R^3$ is methoxy methyl.

In yet another embodiment of the present invention represented by Formula VI, $R^3$ is $C_1$–$C_5$ alkyl.

In another embodiment of the present invention represented by Formula VI, $R^3$ is methyl.

The present invention also includes pharmaceutical compositions that comprise a compound of Formula I, II, III, IV, V, or VI.

Methods of using the compounds of Formula I, II, III, IV, V, or VI include the use of inhibiting nitric oxide synthesis in a subject in need of such inhibition by administering a therapeutically effective amount of the present compound, selectively inhibiting nitric oxide synthesis produced by inducible nitric oxide synthase over nitric oxide produced by the constitutive forms of nitric oxide synthase in a subject in need of such inhibition by administering a therapeutically effective amount of a compound of Formula I, II, III, IV, V, or VI, lowering nitric oxide levels in a subject in need of such by administering a therapeutically effective amount of a compound of Formula I, II, III, IV, V, or VI, lowering nitric oxide levels in a subject in need of such by administering a therapeutically effective amount of a pharmaceutical composition comprising a compound of Formula I, II, III, IV, V, or VI.

The compounds of the present invention may also be used advantageously in combination with a second pharmaceutically active substance, particularly in combination with a selective inhibitor of the inducible isoform of cyclooxygenase (COX-2). Thus, in a further aspect of the invention there is provided the use of a present compound or a pharmaceutically acceptable salt thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a present compound or a pharmaceutically acceptable salt, thereof in combination with a COX-2 inhibitor. COX-2 inhibitors are illustrated but not limited by Celecoxib Vioxx. The NOS inhibitor and the COX-2 inhibitor may either be formulated together within the same pharmaceutical composition for administration in a single dosage unit, or each component may be individually formulated such that separate dosages may be administered either simultaneously or sequentially.

The term "alkyl", alone or in combination, means an acyclic alkyl radical, linear or branched, containing from 1 to 5, or from 1 to 3 carbon atoms. Said alkyl radicals may be optionally substituted with one or more halo.

The terms "alkoxy" embraces linear or branched oxy-containing radicals each having alkyl portions of one to five carbon atoms, such as methoxy radical. Examples of such radicals include methoxy, ethoxy, propoxy, butoxy and tert-butoxy alkyls.

The term "halo" means halogens such as fluorine, chlorine, bromine or iodine atoms.

Also included in the family of compounds of Formula I, II, III, IV, V, or VI are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula I, II, III, IV, V, or VI may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, aralphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula I, II, III, IV, V, or VI include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula I, II, III, IV, V, or VI by reacting, for example, the appropriate acid or base with the compound of Formula I, II, III, IV, V, or VI.

Although nitrogen protecting groups are illustratively shown as, t-butoxycarbonyl, or t-BOC, any suitable nitrogen protecting group could be substituted in the synthesis of the compounds of the present invention. Numerous protected amino groups useful in the present invention for are described by Theodora W. Greene and Peter G. M. Wuts (*Protective Groups in Organic Synthesis*, 3rd ed., John Wiley & Sons, New York, 1999, pp. 494–653). For example NZ can be a 4-chlorobenzylimino group. In one embodiment of the present invention, the protected amino group is any such group resulting from the reaction of an aldehyde with the corresponding amino group to form a Schiff base. A large variety of deprotecting reagents can be advantageously used in the present invention to effect the conversion of the intermediate to the desired compound. Many such deprotecting reagents are described by Greene and Wuts, supra. For example, when the protected amino group is a 4-chlorobenzylimino group or a t-butoxycarbonylamino group, preferably the deprotecting reagent is an acid. Some useful acid deprotecting agents include, without limitation, hydrochloric acid, hydrobromic acid, sulfuric acid, trifluoroacetic acid, phosphoric acid, phosphorus acid, and acetic acid.

When a compound is described by both a structure and a name, the name is intended to correspond to the indicated structure, and similarly the structure is intended to correspond with the indicated name.

While it may be possible for the compounds of Formula I, II, III, IV, V, or VI to be administered as the raw chemical, it is preferable to present them as a pharmaceutical composition. According to a further aspect, the present invention provides a pharmaceutical composition comprising a compound of Formula I, II, III, IV, V, or VI or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of Formula I, II, III, IV, V, or VI or a pharmaceutically acceptable salt or solvate thereof with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 0.5 mg to 200 mg, usually around 0.5 mg to 100 mg.

The compounds of Formula I, II, III, IV, V, or VI are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric, geometric or stereoisomeric forms. The present invention contemplates all such compounds, including cis- and trans-geometric isomers and mixtures thereof, E- and Z-geometric isomers and mixtures thereof, R- and S-enantiomers, diastereomers, d-isomers, l-isomers, the racemic mixtures thereof and other mixtures thereof, as falling within the scope of the invention. Pharmaceutically acceptable salts of such tautomeric, geometric or stereoisomeric forms are also included within the invention.

The terms "cis" and "trans" denote a form of geometric isomerism in which two carbon atoms connected by a double bond will each have two highest ranking groups on the same side of the double bond ("cis" or "Z") or on opposite sides of the double bond ("trans" or "E"). Some of the compounds described contain alkenyl groups, and are meant to include both cis and trans or "E" and "Z" geometric forms. Other compounds of the invention include mixtures of both the cis/Z and the trans/E isomers.

The compounds described contain a stereocenter and are meant to include R, S, and mixtures of R and S forms. Some of the compounds described contain geometric isomers and are meant to include E, Z and mixtures of E and Z forms for each stereocenter present.

The following schemes are useful in making the present invention. Where isomers are not defined, utilization of appropriate chromatography methods will afford single isomers.

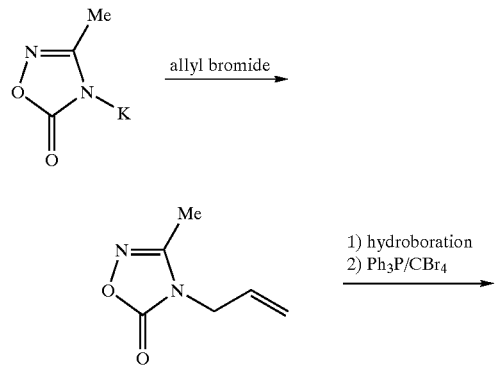

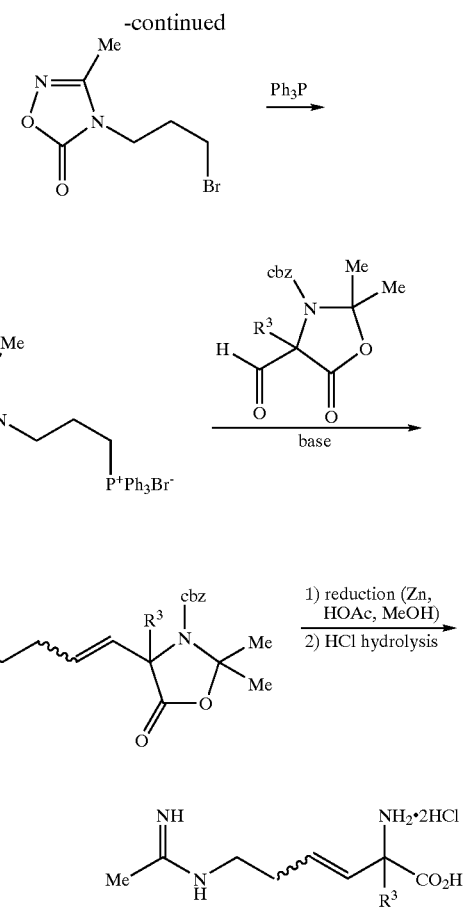

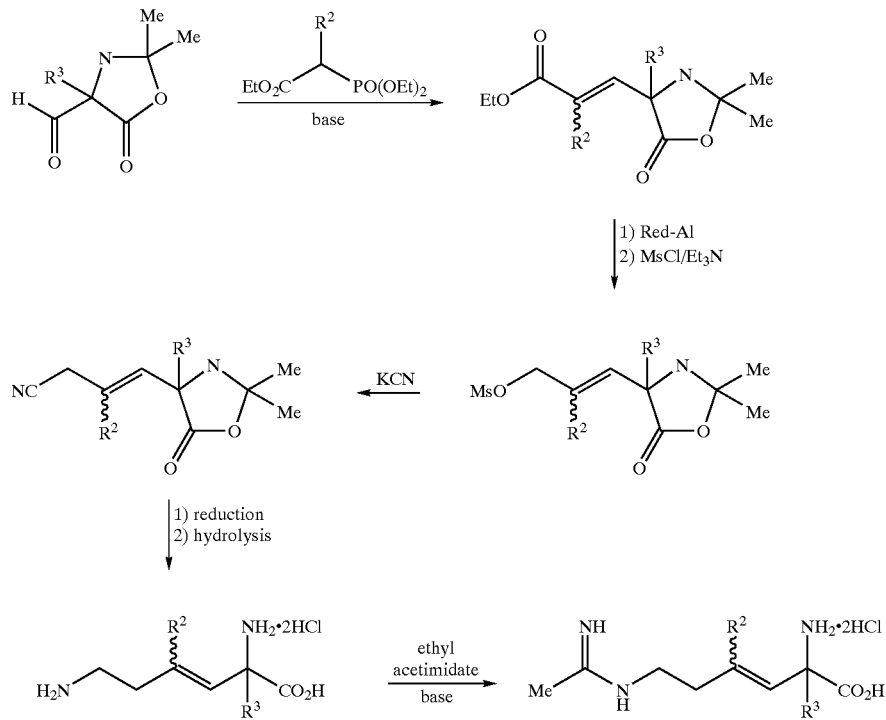

Scheme 3
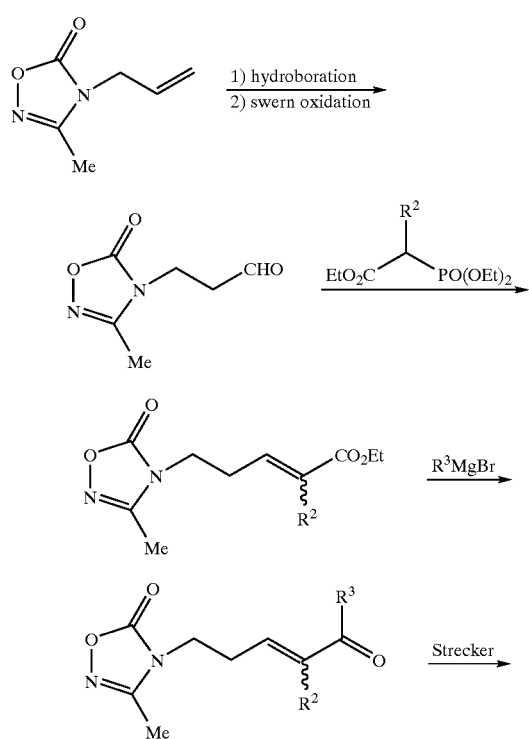
Scheme 4
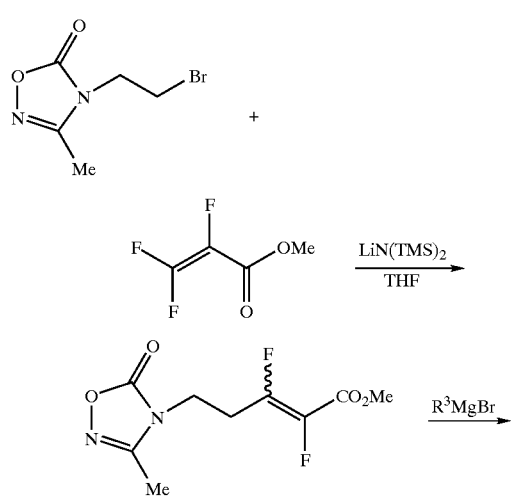
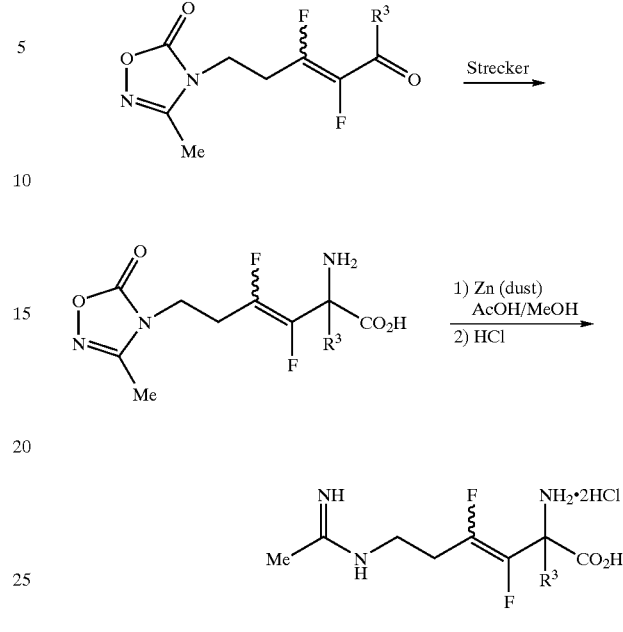
Scheme 5
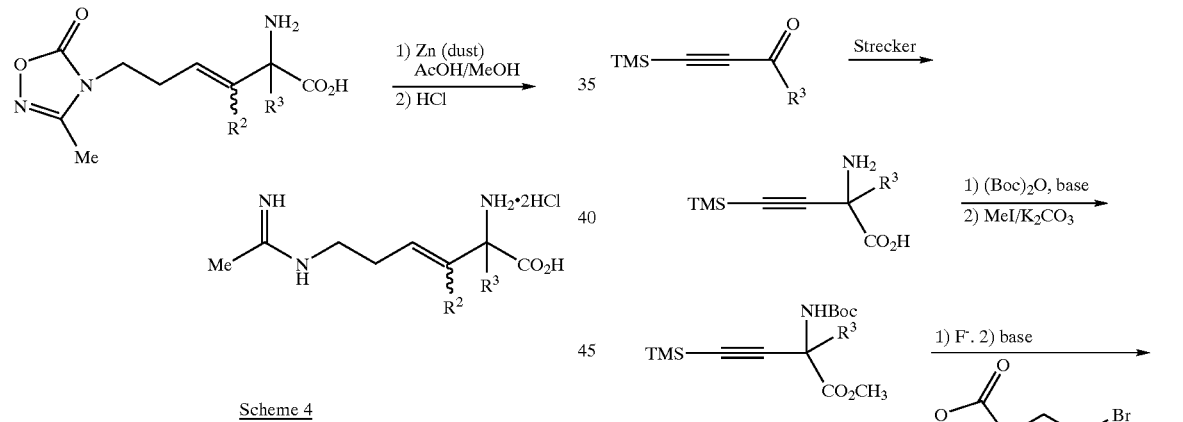

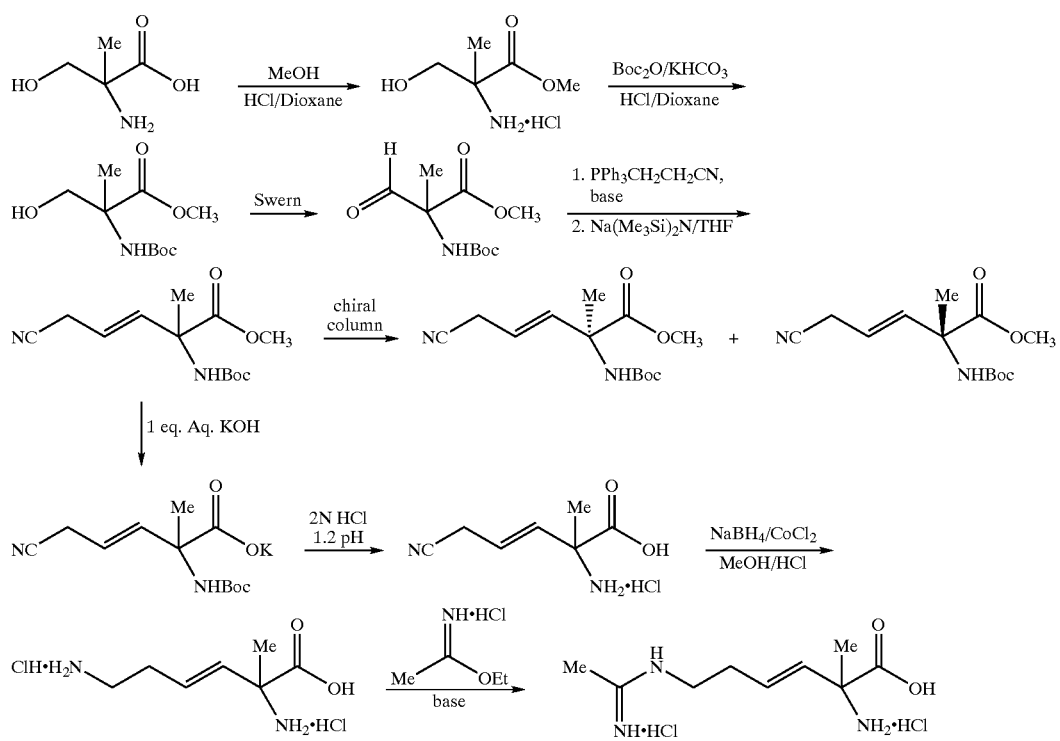

Scheme 6

The following Examples are illustrative of the invention and not intended to limit the scope or breadth.

EXAMPLE 1
(3Z)-2-amino-5-(ethanimidoylamino)-2-methylpent-3-enoic acid dihydrochloride

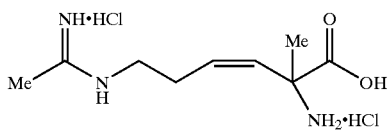

EXAMPLE 1a
Methyl 2-methylserinate hydrochloride

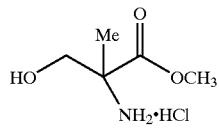

In a three neck 1 L round bottom flask under argon, 2-methylserine (35.0 g, 0.2936 mol) was suspended in methanol (300 mL). To this was added 4N HCl/dioxane (85 mL) and the reaction mixture was stirred at 25° C. for 16 h. The reaction mixture had become a clear colorless solution. Dry HCl gas was bubbled into the reaction mixture for 5 min. and the reaction mixture was then stirred at 60° C. for 4 h. It was then cooled and the excess reagent/solvent was removed under reduced pressure at 65° C. to 70° C. to give the desired product (yield 48.2 g, 96%) as an yellow sticky oil.

Elemental analyses Calcd for $C_5H_{11}NO_3 \cdot 1HCl$: C, 35.41; H, 7.13; N, 8.26; Cl, 20.90. Found for $C_5H_{11}NO_3 + 1.1$ HCl+1.0 $H_2O$: C, 31.62; H, 7.58; N, 7.52; Cl, 19.97.

IR (Neat, λ max $cm^{-1}$): 2959, 1739, 1591.
$^1H$ NMR ($D_2O$, δ ppm): 1.52 (s, 3H), 3.75 (d, 1H), 3.87 (s, 3H), 4.05 (d, 1H).
$^{13}C$ NMR ($D_2O$, δ ppm): 20.63, 56.77, 64.47, 67.19, 174.24.
Mass $(M^{+1})$=134.

EXAMPLE 1b
Methyl N-(tert-butoxycarbonyl)-2-methylserinate

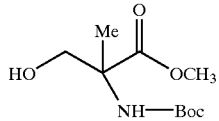

The methyl 2-methylserinate hydrochloride product of Example 1a (16.9 g, 0.1 mol) was dissolved in dioxane/water (120/60 mL) mixture to get a clear colorless solution. To this was added carefully $KHCO_3$ (20.0 g, 0.2 mol) to avoid excess foaming. The reaction mixture was then stirred for 10 min. at 25° C. followed by the addition of $Boc_2O$ (24.0 g, 0.11 mol). This reaction was stirred for 24 h at 25° C. The layers were then separated and the upper layer was taken into EtOAc (200 mL). The lower aqueous layer was extracted with EtOAc (2×40 mL). Both organic layers were combined and dried over anhydrous $MgSO_4$, filtered over celite and evaporated on rotovap at 60° C. to give a clear colorless oil. This crude product was purified by column chromatography using 30% EtOAc in hexane to give the title product as a white solid (yield: 18.0 g, 77%).

Elemental analyses Calcd for $C_{10}H_{19}NO_5$: C, 51.49; H, 8.21; N, 6.00. Found: C, 50.82; H, 8.25; N, 5.32.
IR (Neat, λ max $cm^{-1}$): 2979, 1702, 1499.
$^1H$ NMR ($CDCl_3$, δ ppm): 1.45 (s, 9H), 1.48 (s, 3H), 3.4 (bs, 1H), 3.8 (s, 3H) (m, 2H), 5.3 (bs, 1H).

¹³C NMR (CDCl3, δ ppm): 20.84, 27.40, 27.69, 28.25, 52.74, 66.96, 155.34, 173.91.
Mass (M⁺¹)=234.

EXAMPLE 1c
Methyl 2-[(tert-butoxycarbonyl)amino]-2-methyl-3-oxopropanoate

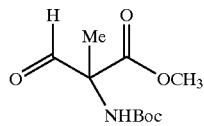

To a stirred solution of oxalyl chloride (2.93 g, 0.0231 mol) in CH₂Cl₂ (30 mL) at −60° C. was added DMSO (3.6 g, 0.0462 mol) during which the reaction temperature rose up to −55° C. The reaction mixture was stirred at this temperature for 10 min. before the addition of a solution of the methyl N-(tert-butoxycarbonyl)-2-methylserinate product of Example 1b (2.7 g, 0.01157 mol) in CH₂Cl₂ (20 mL) at −60° C. The reaction mixture was stirred for additional 20 min., quenched with Et₃N (5.85 g, 0.0578 mol) between −60° C. to −30° C. and filtered. DI water (50 mL) and EtOAc (100 mL) were added to the filtrate and the layers were separated. The organic layer was dried over anhydrous MgSO₄, filtered through Celite and concentrated on a rotovap to give the crude product as an yellow oil. This material was purified by column chromatography using 30% EtOAc in hexane as eluent to give the title product (yield 1.39 g, 49%).

Elemental analyses Calcd for C₁₀H₁₇NO₅: C, 51.94; H, 7.41; N, 6.06. Found for C₁₀H₁₇NO₅+0.3 H₂O: C, 50.87; H, 7.63; N, 5.81.

IR (Neat, λ max cm⁻¹): 2979, 1727, 1706, 1500.
¹H NMR (CDCl₃, δ ppm): 1.4 (s, 9H), 1.7(s, 3H), 3.8 (s, 3H), 5.7 (bs, 1H), 9.6 (s, 1H).
¹³C NMR (CDCl₃, δ ppm): 19.23, 27.69, 28.17, 53.33, 67.99, 169.31, 193.83.
UV, 240 nm, abs 0.072.
Mass (M⁺¹)=232.

EXAMPLE 1d
Methyl (3Z)-2-[(tert-butoxycarbonyl)amino]-5-cyano-2-methylpent-3-enoate

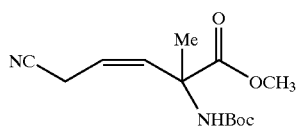

3-Cyanobutyltriphenylphosphonium bromide (0.990 g, 0.0025 mol) is taken up in dry THF (30 mL) and purged with argon. To this sodium is added bis(trimethylsilyl)amide (3 mL 1.0M solution in THF, 0.003 mol) at 20° C. to 25° C. and the reaction mixture is stirred at this temperature for 10 min. After a yellow color change is observed, a solution of the methyl 2-[(tert-butoxycarbonyl)amino]-2-methyl-3-oxopropanoate product of Example 1c (578 mg, 0.0025 mol) in THF (20 mL) is then added and the reaction mixture is stirred under argon for 8 h at 25° C. It is then concentrated on rotovap and the residual mass is taken up in EtOAc (100 mL) and washed with DI water (20 mL). The organic layer is dried over anhydrous MgSO₄, decolorized with activated charcoal (1.0 g), filtered through Celite and concentrated on a rotovap to give crude reaction product as a dark brown oil. Column chromatography of this crude product affords the desired title product.

EXAMPLE 1e
Methyl (3E)-2-[(tert-butoxycarbonyl)amino]-5-cyano-2-methylpent-3-enoate

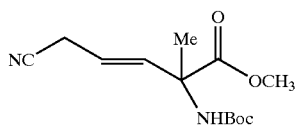

In the preparation of the product of Example 1d, the methyl (3E)-2-[(tert-butoxycarbonyl)amino]-5-cyano-2-methylpent-3-enoate title product is isolated as minor component of the reaction mixture.

EXAMPLE 1f
Methyl (2S,3Z)-2-[(tert-butoxycarbonyl)amino]-5-cyano-2-methylpent-3-enoate

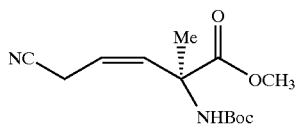

The title compound is isolated by the chiral chromatography of the methyl (3Z)-2-[(tert-butoxycarbonyl)amino]-5-cyano-2-methylpent-3-enoate product of Example 1d.

EXAMPLE 1g
Methyl (2R,3Z)-2-[(tert-butoxycarbonyl)amino]-5-cyano-2-methylpent-3-enoate

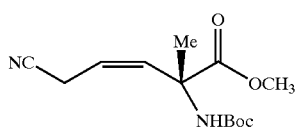

The title compound is isolated by the chiral chromatography of the methyl (3Z)-2-[(tert-butoxycarbonyl)amino]-5-cyano-2-methylpent-3-enoate product of Example 1d.

EXAMPLE 1h
Methyl (2S,3E)-2-[(tert-butoxycarbonyl)amino]-5-cyano-2-methylpent-3-enoate

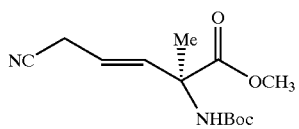

The title compound is isolated by the chiral chromatography of the methyl (3E)-2-[(tert-butoxycarbonyl)amino]-5-cyano-2-methylpent-3-enoate product of Example 1e.

EXAMPLE 1i
Methyl (2R,3E)-2-[(tert-butoxycarbonyl)amino]-5-cyano-2-methylpent-3-enoate

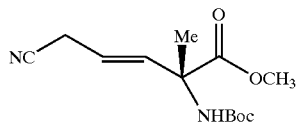

The title compound is isolated by chiral chromatography of the methyl (3E)-2-[(tert-butoxycarbonyl)amino]-5-cyano-2-methylpent-3-enoate product of Example 1e.

EXAMPLE 1j
(3Z)-2-[(tert-butoxycarbonyl)amino]-5-cyano-2-methylpent-3-enoic acid potassium salt

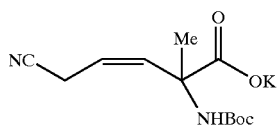

The methyl (3Z)-2-[(tert-butoxycarbonyl)amino]-5-cyano-2-methylpent-3-enoate product of Example 1d is taken up in DI water. To this is added KOH and the reaction mixture is stirred at 50° C. for 3 h. It is then concentrated under reduced pressure to give the desired title product.

EXAMPLE 1k
(3Z)-2-amino-5-cyano-2-methylpent-3-enoic acid hydrochloride

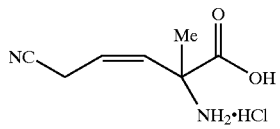

The (3Z)-$^2$-[(tert-butoxycarbonyl)amino]-5-cyano-2-methylpent-3-enoic acid potassium salt product of Example 1j is taken up in DI water (80 mL) containing HCl. The reaction mixture is stirred at 50° C. for 2 h. and concentrated on a rotary evaporator to give the crude product. It is purified using a Gilson chromatographic system to provide the desired title product.

EXAMPLE 11
(3Z)-2,6-diamino-2-methylhex-3-enoic acid dihydrochloride

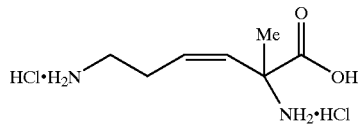

The (3Z)-2-amino-5-cyano-2-methylpent-3-enoic acid hydrochloride product of Example 1k is taken up in MeOH. To this is added Co(II)Cl$_2$.6H$_2$O in one portion with stirring under argon during which the reaction mixture is expected to turn purple. This is followed by the cautious addition of NaBH$_4$ in 6 portions over 15 min. at 25° C. during which the reaction mixture is expected to turn black. HCl is then added carefully and the reaction mixture is stirred until the reaction becomes a light purple color. It is then concentrated under reduced pressure and the residue is subjected to BioRad 'H' form ion exchange resin. Elution with 1% NH$_4$OH/H$_2$O gives the desired fraction. This is concentrated to drive off excess NH$_3$ at <55° C. on a rotary evaporator and then acidified to pH 4.5 with conc. HCl before it is concentrated to dryness to afford the desired title product.

EXAMPLE 1

The (3Z)-2,6-diamino-2-methylhex-3-enoic acid dihydrochloride product of Example 11 is taken up in DI water followed by the addition of 1N NaOH to bring the reaction mixture to pH 8.5. To this solution while stirring is added ethylacetimidate hydrochloride in 6 portions with simultaneous addition of 1N NaOH to maintain the 8.5 pH. Stirring is continued for an additional 20 min. at 25° C. 2N HCl is then added to the reaction mixture until it reaches a pH of 2. The reaction is then concentrated on a rotary evaporator to give the crude product. It is purified chromatographically to afford the desired title product.

EXAMPLE 2
(2S,3E)-2-amino-2-methyl-6-[(1-iminoethyl)amino]-3-hexenoic acid, dihydrochloride

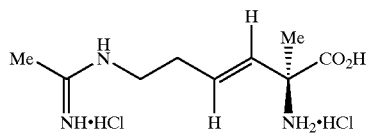

This compound is prepared from the product of Example 1h following the procedures of Examples 1j, 1k, 11, and 1.

EXAMPLE 3
(2S,3Z)-2-amino-2-methyl-6-[(1-iminoethyl)amino]-3-hexenoic acid, dihydrochloride

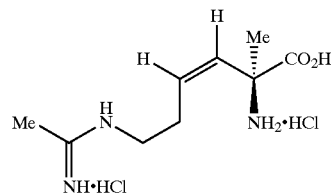

This compound is prepared from the product of Example 1f following the procedures of Examples 1j, 1k, 11, and 1.

EXAMPLE 4
(2R,3E)-2-amino-2-methyl-6-[(1-iminoethyl)amino]-3-hexenoic acid, dihydrochloride

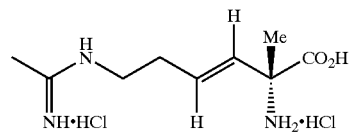

This compound is prepared from the product of Example 1i following the procedures of Examples 1j, 1k, 11, and 1.

EXAMPLE 5
(2R,3Z)-2-amino-2-methyl-6-[(1-iminoethyl)amino]-3-hexenoic acid, dihydrochloride

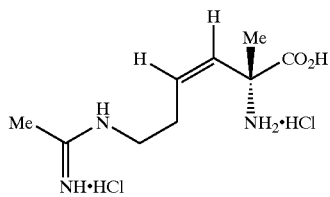

This compound is prepared from the product of Example 1g following the procedures of Examples 1j, 1k, 1l, and 1

EXAMPLE 6
(S,E)-2-amino-2-methyl-4-fluoro-6-[(1-iminoethyl)amino]-3-hexenoic acid, dihydrochloride

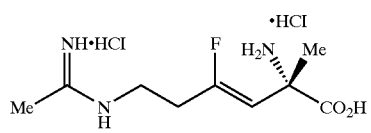

EXAMPLE 7
(S,E)-2-amino-2-methyl-3-fluoro-6-[(1-iminoethyl)amino]-3-hexenoic acid, dihydrochloride

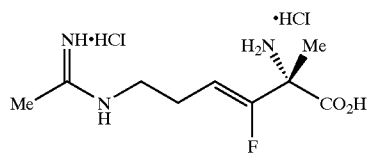

EXAMPLE 8
(S,E)-2-amino-2-methyl-3,4-difluoro-6-[(1-iminoethyl)amino]-3-hexenoic acid, dihydrochloride

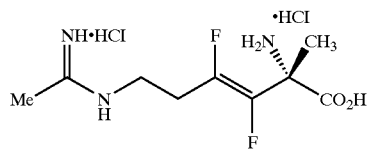

EXAMPLE 9
2-amino-2-methyl-6-[(1-iminoethyl)amino]-3-hexynoic acid, dihydrochloride

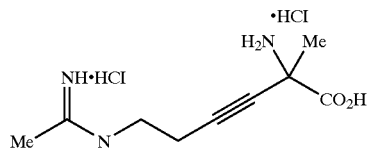

Biological Data

Some or all of the following assays are used to demonstrate the nitric oxide synthase inhibitory activity of the invention's compounds as well as demonstrate the useful pharmacological properties.

Citrulline Assay for Nitric Oxide Synthase

Nitric oxide synthase (NOS) activity can be measured by monitoring the conversion of L-[2,3-$^3$H]-arginine to L-[2,3-$^3$H]-citrulline (Bredt and Snyder, *Proc. Natl. Acad. Sci. U.S.A.*, 87, 682–685, 1990 and Moore et al, *J. Med. Chem.*, 39 669–672, 1996). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a λcDNA library made from RNA extracted from a colon sample from a patient with ulcerative colitis. The cDNA for human endothelial constitutive NOS (hecNOS) is isolated from a λcDNA library made from RNA extracted from human umbilical vein endothelial cells (HUvEC) and the cDNA for human neuronal constitutive NOS (hncNOS) is isolated from a λcDNA library made from RNA extracted from human cerebellum obtained from a cadaver. The recombinant enzymes are expressed in Sf9 insect cells using a baculovirus vector (Rodi et al, in *The Biology of Nitric Oxide, Pt. 4: Enzymology, Biochemistry and Immunology*: Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 μL of enzyme is added to 40 μL of 50 mM Tris (pH 7.6) in the presence or absence of test compounds and the reaction initiated by the addition of 50 μL of a reaction mixture containing 50 mM Tris (pH 7.6), 2.0 mg/mL bovine serum albumin, 2.0 mM DTT, 4.0 mM $CaCl_2$, 20 μM FAD, 100 μM tetrahydrobiopterin, 0.4 mM NADPH and 60 μM L-arginine containing 0.9 μCi of L-[2,3-$^3$H]-arginine. The final concentration of L-arginine in the assay is 30 μM. For hecNOS or hncNOS, calmodulin is included at a final concentration of 40–100 nM. Following incubation at 37° C. for 15 minutes, the reaction is terminated by addition of 400 μL of a suspension (1 part resin, 3 parts buffer) of Dowex 50W X-8 cation exchange resin (sodium form) in a stop buffer containing 10 mM EGTA, 100 mM BEPES, pH 5.5 and 1 mM L-citrulline. After mixing the resin is allowed to settle and L-[2,3-$^3$H]-Citrulline formation is determined by counting aliquots of the supernatant with a liquid scintillation counter. $IC_{50}$ values can be determined by testing each compound at several concentrations. Results are reported as the $IC_{50}$ values of compounds for hiNOS, hecNOS and hncNOS.

In vivo Assay

Rats can be treated with an intraperitoneal injection of 1–12.5 mg/kg of endotoxin (LPS) to induce systemic expression of inducible nitric oxide synthase, resulting in markedly elevated plasma nitrite/nitrate levels. Compounds are administered orally 0.5–1 hours prior to LPS administration and plasma nitrite/nitrate levels are determined 5 hours following LPS administration. The results can be used to show that the administration of the nitric oxide synthase inhibitors decreases the rise in plasma nitrite/nitrate levels, a reliable indicator of the production of nitric oxide induced by endotoxin. $ED_{50}$ values (mg/kg) for inhibition of the LPS-induced increase in plasma nitrite/nitrate levels can be determined.

Raw Cell Nitrite Assay

RAW 264.7 cells can be plated to confluency on a 96-well tissue culture plate grown overnight (17 h) in the presence of LPS to induce NOS. A row of 3–6 wells can be left untreated and serve as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 μL of buffer containing L-arginine (30 μM) +/– inhibitors for 1 h. The assay can be initiated by warming the plate to 37° C. in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite (T. P. Misko et al, *Analytical Biochemistry*, 214, 11–16, 1993).

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage is cut into small explants of approximately 15–45 mg in weight and one or two explants per well are placed into either 96 or 48 well culture plates with 200–500 μL of culture media per well. The culture media was either a custom modification of Minimum Essential Medium(Eagle) with Earle's salts (GibcoBRL) prepared without L-Arginine, without L-Glutamine and without phenol red or a custom modification of serumless Neuman and Tytell (GibcoBRL) medium prepared without L-arginine, without insulin, without ascorbic acid, without L-glutamine and without phenol red. Both are supplemented before use with 100 μM L-Arginine (Sigma), 2 mM L-glutamine, 1× HL-1 supplement (BioWhittaker), 50 mg/ml ascorbic acid (Sigma) and 150 μg/ml recombinant human IL-1β (RD Systems) to induce nitric oxide synthase. Compounds are then added in 10 μL aliquots and the explants incubated at 37° C. with 5% $CO_2$ for 18–24 hours.

The day old supernatant is then discarded and replaced with fresh culture media containing recombinant human IL-1, and compound and incubated for another 20–24 hours. This supernatant is analyzed for nitrite with a fluorometric assay (Misko et al, *Anal. Biochem.*, 214, 11–16, 1993). All samples are done in quadruplicate. Unstimulated controls are cultured in media in the absence of recombinant human IL-1β. $IC_{50}$ values are determined from plotting the percent inhibition of nitrite production at six different concentrations of inhibitor.

Assay for Time Dependent Inhibition

Compounds are evaluated for time dependent inhibition of human NOS isoforms by preincubation of the compound with the enzyme at 37° C. in the presence of the citrulline enzyme assay components, minus L-arginine, for times ranging from 0–60 minutes. Aliquots (10 μL) are removed at 0, 10, 21 and 60 minutes and immediately added to a citrulline assay enzyme reaction mixture containing L-[2,3-$^3$H]-arginine and a final L-arginine concentration of 30 μM in a final volume of 100 μL. The reaction is allowed to proceed for 15 minutes at 37° C. and terminated by addition of a suspension of Dowex 50W X-8 cation exchange ion resin as described above for the citrulline NOS assay. The % inhibition of NOS activity by an inhibitor is taken as the per cent inhibition in activity compared to control enzyme preincubated for the same time in the absence of inhibitor. Time-dependent inhibition can be demonstrated as an increase in inhibition with increasing preincubation time.

What is claimed:
1. A compound of Formula I:

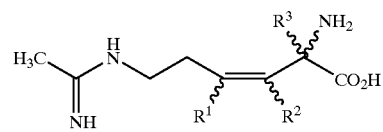

or a pharmaceutically acceptable salt thereof, wherein:
The compound is the Z isomer, and wherein:
$R^1$ is hydrogen;
$R^2$ is fluorine; and
$R^3$ is methyl.

2. A compound of Formula I:

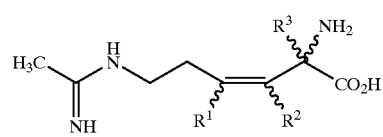

or a pharmaceutically acceptable salt thereof, wherein:
The compound is the Z isomer, and wherein:
$R^1$ is halo;
$R^2$ is selected from the group consisting of hydrogen, halo and $C_1$–$C_3$ alkyl; and
$R^3$ is $C_1$–$C_3$ alkyl.

3. The compound of claim 2 wherein:
$R^1$ is halo;
$R^2$ is halo; and
$R^3$ is $C_1$–$C_3$ alkyl.

4. The compound of claim 3 wherein:
$R^1$ is fluorine;
$R^2$ is fluorine; and
$R^3$ is methyl.

5. The compound of claim 2 wherein:
$R^1$ is fluorine;
$R^2$ is selected from the group consisting of hydrogen and $C_1$–$C_3$ alkyl; and
$R^3$ is methyl.

6. The compound of claim 5 wherein:
$R^1$ is fluorine;
$R^2$ is hydrogen; and
$R^3$ is methyl.

7. A compound of Formula I:

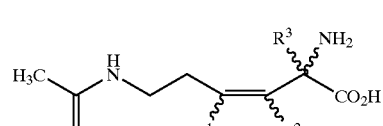

or a pharmaceutically acceptable salt thereof, wherein:
The compound is the Z isomer, and wherein:
$R^1$ is hydrogen;
$R^2$ is $CH_2F$; and
$R^3$ is methyl.

8. A compound of Formula I:

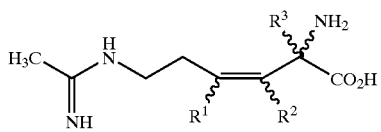

or a pharmaceutically acceptable salt thereof, wherein:
The compound is the Z isomer, and wherein:
$R^1$ is $CH_2F$;
$R^2$ is hydrogen; and
$R^3$ is methyl.

9. A compound of Formula I:

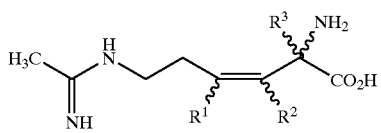

or a pharmaceutically acceptable salt thereof, wherein:
The compound is the Z isomer, and wherein:
$R^1$ is hydrogen;
$R^2$ is hydrogen; and
$R^3$ is $CH_2F$.

10. A compound of Formula I:

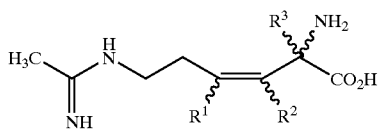

or a pharmaceutically acceptable salt thereof, wherein:
The compound is the Z isomer, and wherein:
$R^1$ is hydrogen;
$R^2$ is methoxymethyl; and
$R^3$ is methyl.

11. A compound of Formula I:

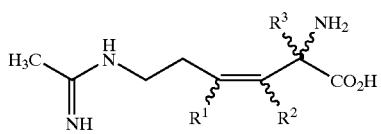

or a pharmaceutically acceptable salt thereof, wherein:
The compound is the Z isomer, and wherein:
$R^1$ is methoxymethyl;
$R^2$ is hydrogen; and
$R^3$ is methyl.

12. A compound of Formula I:

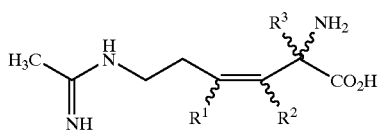

or a pharmaceutically acceptable salt thereof, wherein:
The compound is the Z isomer, and wherein:
$R^1$ is hydrogen;
$R^2$ is hydrogen; and
$R^3$ is methoxymethyl.

13. A compound of Formula I:

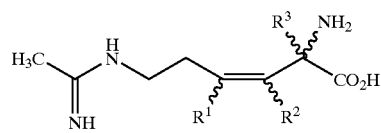

or a pharmaceutically acceptable salt thereof, wherein:
The compound is the E isomer, and wherein
$R^1$ is hydrogen;
$R^2$ is fluorine; and
$R^3$ is methyl.

14. A compound of Formula I:

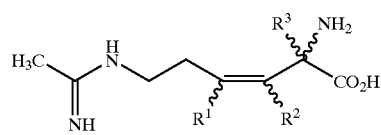

or a pharmaceutically acceptable salt thereof, wherein:
The compound is the E isomer, and wherein
$R^1$ is halo;
$R^2$ is selected from the group consisting of hydrogen, halo and $C_1$–$C_3$ alkyl; and
$R^3$ is $C_1$–$C_3$ alkyl.

15. The compound of claim 14 wherein:
$R^1$ is halo;
$R^2$ is halo; and
$R^3$ is $C_1$–$C_3$ alkyl.

16. The compound of claim 15 wherein:
$R^1$ is fluorine;
$R^2$ is fluorine; and
$R^3$ is methyl.

17. The compound of claim 14 wherein:
$R^1$ is fluorine;
$R^2$ is selected from the group consisting of hydrogen and $C_1$–$C_3$ alkyl; and
$R^3$ is methyl.

18. The compound of claim 17 wherein:
$R^1$ is fluorine;
$R^2$ is hydrogen; and
$R^3$ is methyl.

19. A compound of Formula I:

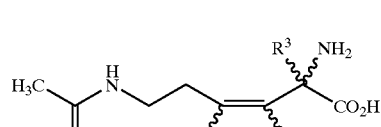

or a pharmaceutically acceptable salt thereof, wherein:
The compound is the E isomer, and wherein
$R^1$ is methyl;
$R^2$ is hydrogen; and
$R^3$ is methyl.

20. A compound of Formula I:

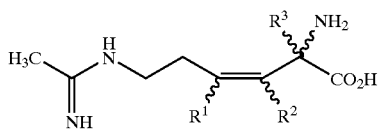

or a pharmaceutically acceptable salt thereof, wherein:

The compound is the E isomer, and wherein
$R^1$ is hydrogen;
$R^2$ is methyl; and
$R^3$ is methyl.

21. A compound of Formula I:

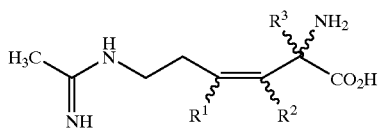

or a pharmaceutically acceptable salt thereof, wherein:

The compound is the E isomer, and wherein
$R^1$ is methyl;
$R^2$ is methyl; and
$R^3$ is methyl.

22. A compound of Formula I:

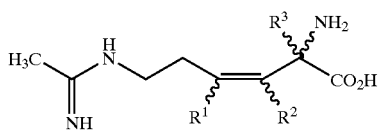

or a pharmaceutically acceptable salt thereof, wherein:

The compound is the E isomer, and wherein
$R^1$ is selected from the group consisting of hydrogen and fluorine;
$R^2$ is $C_1$–$C_3$ alkyl substituted by one or more halo; and
$R^3$ is methyl.

23. A compound of Formula I:

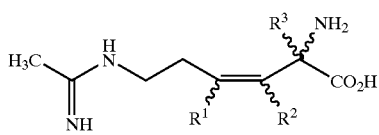

or a pharmaceutically acceptable salt thereof, wherein:

The compound is the E isomer; and wherein:
$R^1$ is hydrogen;
$R^2$ is $CH_2F$; and
$R^3$ is methyl.

24. A compound of Formula I:

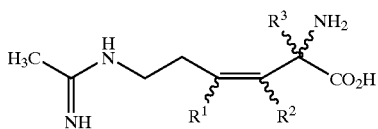

or a pharmaceutically acceptable salt thereof, wherein:
The compound is the E isomer, and wherein:
$R^1$ is $CH_2F$;
$R^2$ is hydrogen; and
$R^3$ is methyl.

25. A compound of Formula I:

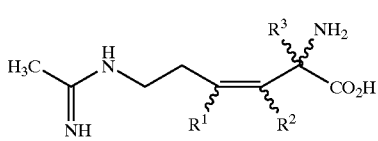

or a pharmaceutically acceptable salt thereof, wherein:
The compound is the E isomer, and wherein:
$R^1$ is hydrogen;
$R^2$ is hydrogen; and
$R^3$ is $CH_2F$.

26. A compound of Formula I:

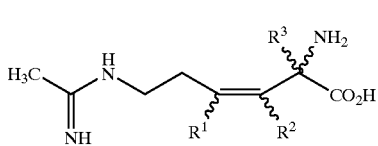

The compound is the E isomer, and wherein:
$R^1$ is hydrogen;
$R^2$ is methoxymethyl; and
$R^3$ is methyl.

27. A compound of Formula I:

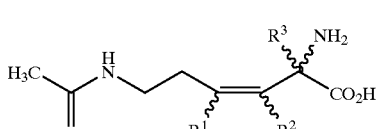

or a pharmaceutically acceptable salt thereof, wherein:
The compound is the E isomer, and wherein:
$R^1$ is methoxymethyl;
$R^2$ is hydrogen; and
$R^3$ is methyl.

28. A compound of Formula I:

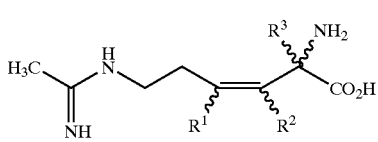

or a pharmaceutically acceptable salt thereof, wherein:
The compound is the E isomer; and wherein:
$R^1$ is hydrogen;
$R^2$ is hydrogen; and
$R^3$ is methoxymethyl.

29. A compound of Formula II

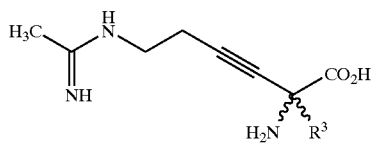

or a pharmaceutically acceptable salt thereof, wherein:
$R^3$ is $C_1$–$C_5$ alkyl substituted by one or more halo.
30. The compound of claim 29 wherein:
$R^3$ is $C_1$–$C_5$ alkyl substituted by one or more fluorine.
31. The compound of claim 29 wherein:
$R^3$ is methyl substituted by one or more halo.
32. The compound of claim 31 wherein:
$R^3$ is methyl substituted by one or more fluorine.
33. The compound of claim 31 wherein:
$R^3$ is $CH_2F$.
34. A compound of Formula II

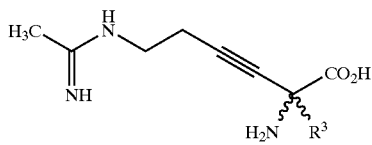

or a pharmaceutically acceptable salt thereof, wherein:
wherein:
$R^3$ is $C_1$–$C_5$ alkyl substituted by alkoxy.
35. The compound of claim 34 wherein:
$R^3$ is methoxy methyl.
36. A compound of Formula III

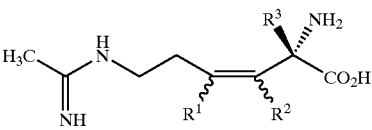

or a pharmaceutically acceptable salt thereof, wherein:
The compound is the Z isomer, and wherein:
$R^1$ is hydrogen;
$R^2$ is fluorine; and
$R^3$ is methyl.
37. A compound of Formula III

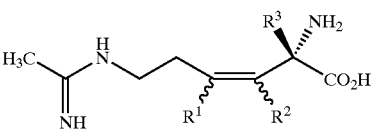

or a pharmaceutically acceptable salt thereof, wherein:
The compound is the Z isomer, and wherein
$R^1$ is halo;
$R^2$ is selected from the group consisting of hydrogen, halo and $C_1$–$C^3$ alkyl; and
$R^3$ is $C_1$–$C_3$ alkyl.
38. The compound of claim 37 wherein:
$R^1$ is halo;
$R^2$ is halo; and
$R^3$ is $C_1$–$C_3$ alkyl.

39. The compound of claim 38 wherein:
$R^1$ is fluorine;
$R^2$ is fluorine; and
$R^3$ is methyl.
40. The compound of claim 37 wherein:
$R^1$ is fluorine;
$R^2$ is selected from the group consisting of hydrogen and $C_1$–$C_3$ alkyl; and
$R^3$ is methyl.
41. The compound of claim 40 wherein:
$R^1$ is fluorine;
$R^2$ is hydrogen; and
$R^3$ is methyl.
42. A compound of Formula III

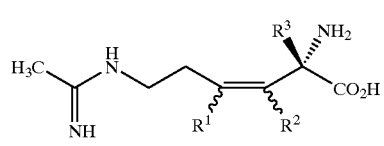

or a pharmaceutically acceptable salt thereof, wherein:
The compound is the Z isomer, and wherein
$R^1$ is methyl;
$R^2$ is hydrogen; and
$R^3$ is methyl.
43. A compound of Formula III

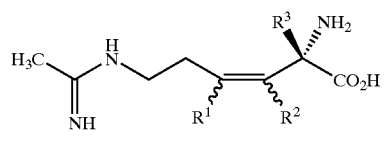

or a pharmaceutically acceptable salt thereof, wherein:
The compound is the Z isomer, and wherein:
$R^1$ is hydrogen;
$R^2$ is methyl; and
$R^3$ is methyl.
44. A compound of Formula III

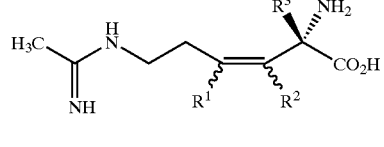

or a pharmaceutically acceptable salt thereof, wherein:
The compound is the Z isomer, and wherein:
$R^1$ is methyl;
$R^2$ is methyl; and
$R^3$ is methyl.
45. A compound of Formula III

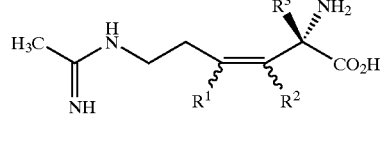

or a pharmaceutically acceptable salt thereof, wherein:
The compound is the Z isomer, and wherein
$R^1$ is selected from the group consisting of hydrogen and fluorine;
$R^2$ is $C_1$–$C_3$ alkyl substituted by one or more halo; and
$R^3$ is methyl.

46. The compound of claim 45 wherein:
$R^1$ is hydrogen;
$R^2$ is $CH_2F$; and
$R^3$ is methyl.

47. A compound of Formula III

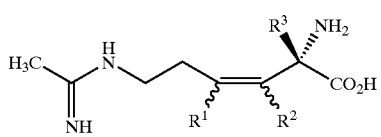

III or a pharmaceutically acceptable salt thereof, wherein:
The compound is the Z isomer, and wherein
$R^1$ is $CH_2F$;
$R^2$ is hydrogen; and
$R^3$ is methyl.

48. A compound of Formula III

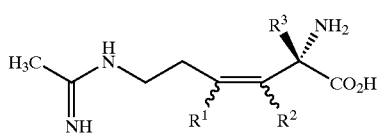

III or a pharmaceutically acceptable salt thereof, wherein:
The compound is the Z isomer, and wherein
$R^1$ is hydrogen;
$R^2$ is hydrogen; and
$R^3$ is $CH_2F$.

49. A compound of Formula III

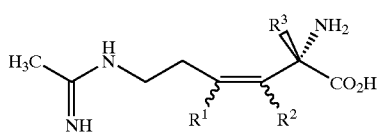

III or a pharmaceutically acceptable salt thereof, wherein:
The compound is the Z isomer, and wherein
$R^1$ is hydrogen;
$R^2$ is methoxymethyl; and
$R^3$ is methyl.

50. A compound of Formula III

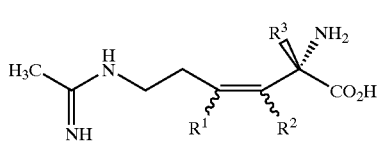

III or a pharmaceutically acceptable salt thereof, wherein:
The compound is the Z isomer, and wherein
$R^1$ is methoxymethyl;
$R^2$ is hydrogen; and
$R^3$ is methyl.

51. A compound of Formula III

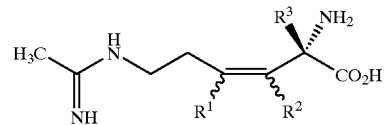

III or a pharmaceutically acceptable salt thereof, wherein:
The compound is the Z isomer, and wherein
$R^1$ is hydrogen;
$R^2$ is hydrogen; and
$R^3$ is methoxymethyl.

52. A compound of Formula III

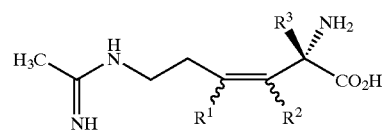

III or a pharmaceutically acceptable salt thereof, wherein:
The compound is the E isomer, and wherein:
$R^1$ is hydrogen;
$R^2$ is fluorine; and
$R^3$ is methyl.

53. A compound of Formula III

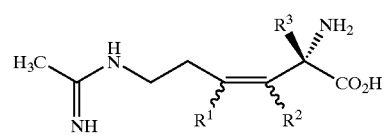

III or a pharmaceutically acceptable salt thereof, wherein:
The compound is the E isomer, and wherein:
$R^1$ is halo;
$R^2$ is selected from the group consisting of hydrogen, halo and $C_1$–$C_3$ alkyl; and
$R^3$ is $C_1$–$C_3$ alkyl.

54. The compound of claim 53 wherein:
$R^1$ is halo;
$R^2$ is halo; and
$R^3$ is $C_1$–$C_3$ alkyl.

55. The compound of claim 54 wherein:
$R^1$ is fluorine;
$R^2$ is fluorine; and
$R^3$ methyl.

56. The compound of claim 53 wherein:
$R^1$ is fluorine;
$R^2$ is selected from the group consisting of hydrogen and $C_1$–$C_3$ alkyl; and
$R^3$ is methyl.

57. The compound of claim 56 wherein:
$R^1$ is fluorine;
$R^2$ is hydrogen; and
$R^3$ is methyl.

58. A compound of Formula III

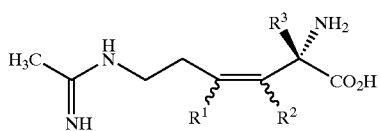

or a pharmaceutically acceptable salt thereof, wherein:
The compound is the E isomer, and wherein:
$R^1$ is hydrogen;
$R^2$ is $CH_2F$; and
$R^3$ is methyl.

59. A compound of Formula III

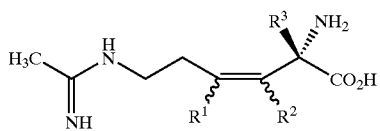

or a pharmaceutically acceptable salt thereof, wherein:
The compound is the E isomer, and wherein:
$R^1$ is $CH_2F$;
$R^2$ is hydrogen; and
$R^3$ is methyl.

60. A compound of Formula III

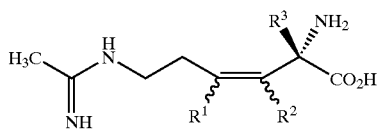

or a pharmaceutically acceptable salt thereof, wherein:
The compound is the E isomer, and wherein:
$R^1$ is hydrogen;
$R^2$ is hydrogen; and
$R^3$ is $CH_2F$.

61. A compound of Formula III

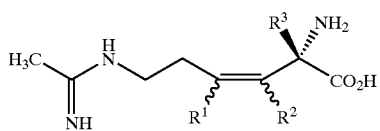

or a pharmaceutically acceptable salt thereof, wherein:
The compound is the E isomer, and wherein:
$R^1$ is hydrogen;
$R^2$ is methoxymethyl; and
$R^3$ is methyl.

62. A compound of Formula III

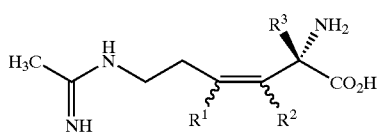

or a pharmaceutically acceptable salt thereof, wherein:
The compound is the E isomer, and wherein:
$R^1$ is methoxymethyl;
$R^2$ is hydrogen; and
$R^3$ is methyl.

63. A compound of Formula III

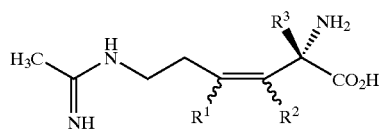

or a pharmaceutically acceptable salt thereof, wherein:
The compound is the E isomer, and wherein:
$R^1$ is hydrogen;
$R^2$ is hydrogen; and
$R^3$ is methoxymethyl.

64. A compound of Formula IV

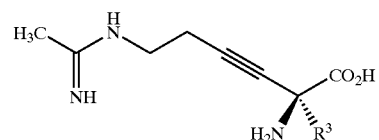

or a pharmaceutically acceptable salt thereof, wherein:
$R^3$ is $C_1$–$C_5$ alkyl substituted by one or more halo.

65. The compound of claim 64 wherein:
$R^3$ is $C_1$–$C_5$ alkyl substituted by one or more fluorine.

66. The compound of claim 64 wherein:
$R^3$ is methyl substituted by one or more halo.

67. The compound of claim 66 wherein:
$R^3$ is methyl substituted by one or more fluorine.

68. The compound of claim 66 wherein:
$R^3$ is $CH_2F$.

69. A compound of Formula IV

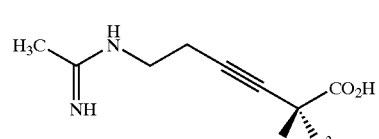

or a pharmaceutically acceptable salt thereof, wherein:
$R^3$ is $C_1$–$C_5$ alkyl substituted by alkoxy.

70. The compound of claim 69 wherein:
$R^3$ is methoxy methyl.

71. A compound of Formula V

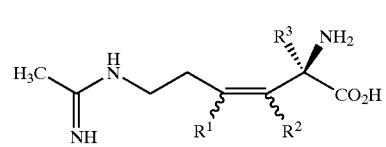

or a pharmaceutically acceptable salt thereof, wherein:
The compound is the Z isomer, and wherein:
$R^1$ is hydrogen;
$R^2$ is fluorine; and
$R^3$ is methyl.

72. A compound of Formula V

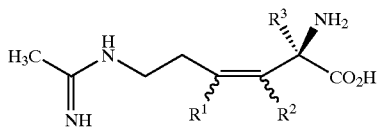

or a pharmaceutically acceptable salt thereof, wherein:
The compound is the Z isomer, and wherein:
$R^1$ is halo;
$R^2$ is selected from the group consisting of hydrogen, halo and $C_1-C_3$ alkyl; and
$R^3$ is $C_1-C_3$ alkyl.

73. The compound of claim 72 wherein:
$R^1$ is halo;
$R^2$ is halo; and
$R^3$ is $C_1-C_3$ alkyl.

74. The compound of claim 73 wherein:
$R^1$ is fluorine;
$R^2$ is fluorine; and
$R^3$ is methyl.

75. The compound of claim 72 wherein:
$R^1$ is fluorine;
$R^2$ is selected from the group consisting of hydrogen and $C_1-C_3$ alkyl; and
$R^3$ is methyl.

76. The compound of claim 75 wherein:
$R^1$ is fluorine;
$R^2$ is hydrogen; and
$R^3$ is methyl.

77. A compound of Formula V

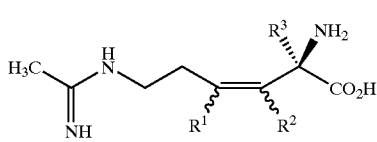

or a pharmaceutically acceptable salt thereof, wherein:
The compound is the Z isomer, and wherein:
$R^1$ is selected from the group consisting of hydrogen and fluorine;
$R^2$ is $C_1-C_3$ alkyl substituted by one or more halo; and
$R^3$ is methyl.

78. The compound of claim 77 wherein:
$R^1$ is hydrogen;
$R^2$ is $CH_2F$; and
$R^3$ is methyl.

79. A compound of Formula V

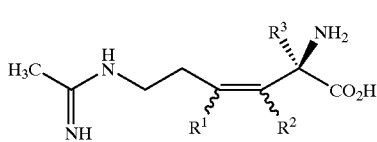

or a pharmaceutically acceptable salt thereof, wherein:
The compound is the Z isomer, and wherein:
$R^1$ is $CH_2F$;
$R^2$ is hydrogen; and
$R^3$ is methyl.

80. A compound of Formula V

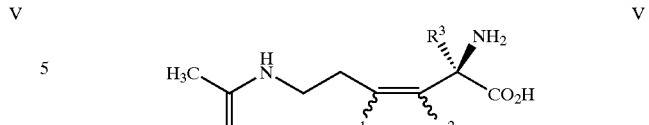

or a pharmaceutically acceptable salt thereof, wherein:
The compound is the Z isomer, and wherein:
$R^1$ is hydrogen;
$R^2$ is hydrogen; and
$R^3$ is $CH_2F$.

81. A compound of Formula V

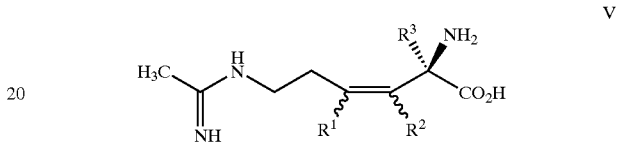

or a pharmaceutically acceptable salt thereof, wherein:
The compound is the Z isomer, and wherein:
$R^1$ is hydrogen;
$R^2$ is methoxymethyl; and
$R^3$ is methyl.

82. A compound of Formula V

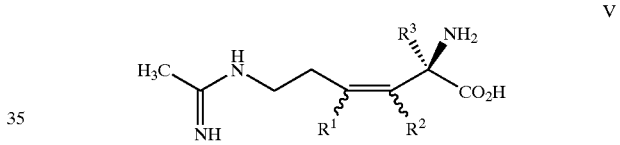

or a pharmaceutically acceptable salt thereof, wherein:
The compound is the Z isomer, and wherein:
$R^1$ is methoxymethyl;
$R^2$ is hydrogen; and
$R^3$ is methyl.

83. A compound of Formula V

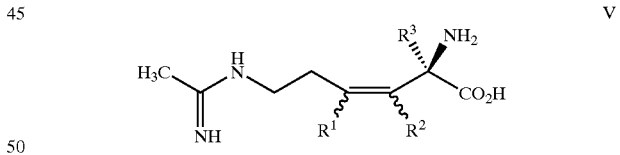

or a pharmaceutically acceptable salt thereof, wherein:
The compound is the Z isomer, and wherein:
$R^1$ is hydrogen;
$R^2$ is hydrogen; and
$R^3$ is methoxymethyl.

84. A compound of Formula V

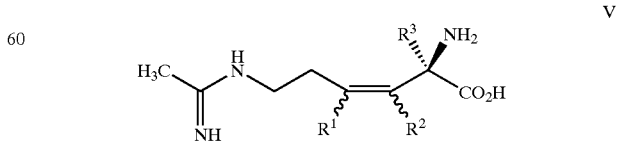

or a pharmaceutically acceptable salt thereof, wherein:
The compound is the E isomer, and wherein::

$R^1$ is hydrogen;
$R^2$ is fluorine; and
$R^3$ is methyl.

85. A compound of Formula V

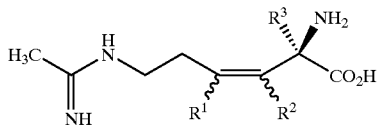

V or a pharmaceutically acceptable salt thereof, wherein:

The compound is the E isomer, and wherein:
$R^1$ is halo;
$R^2$ is selected from the group consisting of hydrogen, halo and $C_1$–$C_3$ alkyl; and
$R^3$ is $C_1$–$C_3$ alkyl.

86. The compound of claim 85 wherein:
$R^1$ is halo;
$R^2$ is halo; and
$R^3$ is $C_1$–$C_3$ alkyl.

87. The compound of claim 86 wherein:
$R^1$ is fluorine;
$R^2$ is fluorine; and
$R^3$ is methyl.

88. The compound of claim 85 wherein:
$R^1$ is fluorine;
$R^2$ is selected from the group consisting of hydrogen and $C_1$–$C_3$ alkyl; and
$R^3$ is methyl.

89. The compound of claim 88 wherein:
$R^1$ is fluorine;
$R^2$ is hydrogen; and
$R^3$ is methyl.

90. A compound of Formula V

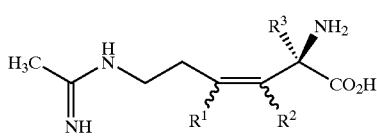

V or a pharmaceutically acceptable salt thereof, wherein:

The compound is the E isomer, and wherein:
$R^1$ is selected from the group consisting of hydrogen and fluorine;
$R^2$ is $C_1$–$C_3$ alkyl substituted by one or more halo; and
$R^3$ is methyl.

91. The compound of claim 90 wherein:
$R^1$ is hydrogen;
$R^2$ is $CH_2F$; and
$R^3$ is methyl.

92. The compound of claim 90 wherein:
$R^1$ is $CH_2F$;
$R^2$ is hydrogen; and
$R^3$ is methyl.

93. A compound of Formula V

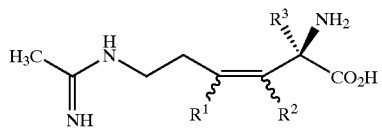

V or a pharmaceutically acceptable salt thereof, wherein:
The compound is the E isomer, and wherein:
$R^1$ is hydrogen;
$R^2$ is hydrogen; and
$R^3$ is $CH_2F$.

94. A compound of Formula V

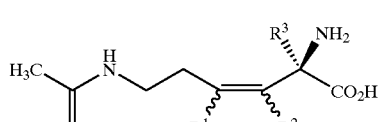

V or a pharmaceutically acceptable salt thereof, wherein:
The compound is the E isomer, and wherein:
$R^1$ is hydrogen;
$R^2$ is methoxymethyl; and
$R^3$ is methyl.

95. A compound of Formula V

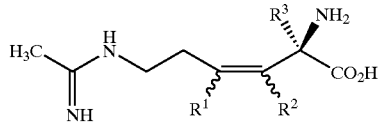

V or a pharmaceutically acceptable salt thereof, wherein:
The compound is the E isomer, and wherein:
$R^1$ is methoxymethyl;
$R^2$ is hydrogen; and
$R^3$ is methyl.

96. A compound of Formula V

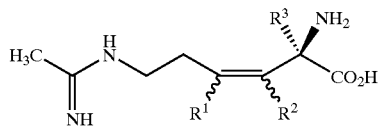

V or a pharmaceutically acceptable salt thereof, wherein:
The compound is the E isomer, and wherein:
$R^1$ is hydrogen;
$R^2$ is hydrogen; and
$R^3$ is methoxymethyl.

97. A compound of Formula VI

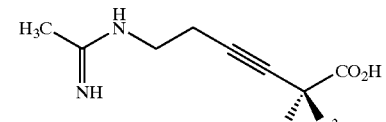

VI or a pharmaceutically acceptable salt thereof, wherein:
$R^3$ is $C_1$–$C_5$ alkyl substituted by one or more halo.

98. The compound of claim 97 wherein:
$R^3$ is $C_1$–$C_5$ alkyl substituted by one or more fluorine.

99. The compound of claim 97 wherein:
$R^3$ is methyl substituted by one or more halo.

100. The compound of claim 99 wherein:
$R^3$ is methyl substituted by one or more fluorine.
101. The compound of claim 99 wherein:
$R^3$ is $CH_2F$.
102. A compound of Formula VI
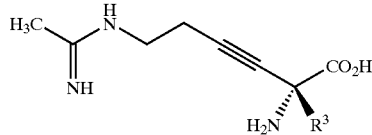
VI
or a pharmaceutically acceptable salt thereof, wherein:
$R^3$ is $C_1$–$C_5$ alkyl substituted by alkoxy.
103. The compound of claim 102 wherein:
$R^3$ is methoxy methyl.
104. A novel intermediate compound selected from:
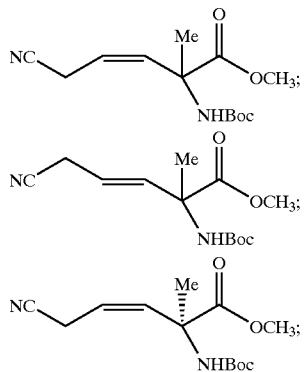
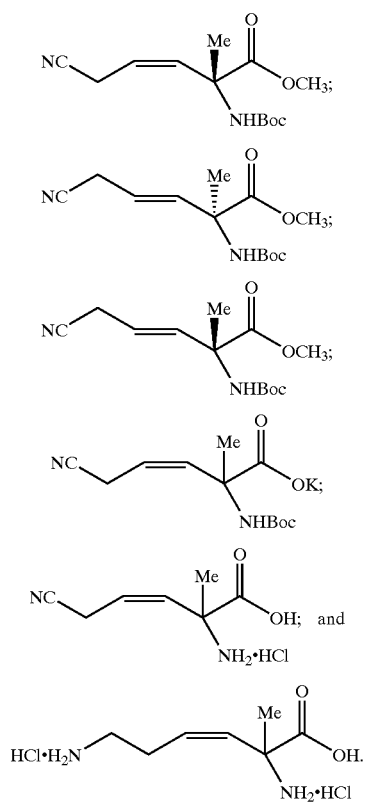
* * * * *